US008579879B2

(12) United States Patent
Palerm et al.

(10) Patent No.: US 8,579,879 B2
(45) Date of Patent: Nov. 12, 2013

(54) CLOSED-LOOP GLUCOSE CONTROL STARTUP

(75) Inventors: Cesar C. Palerm, Pasadena, CA (US); Anirban Roy, Encino, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 668 days.

(21) Appl. No.: 12/709,437

(22) Filed: Feb. 19, 2010

(65) Prior Publication Data

US 2011/0208155 A1 Aug. 25, 2011

(51) Int. Cl.
*A61M 31/00* (2006.01)
(52) U.S. Cl.
USPC .......................................... 604/503
(58) Field of Classification Search
USPC .......................................... 604/503
See application file for complete search history.

(56) References Cited

U.S. PATENT DOCUMENTS

| 5,391,250 | A | 2/1995 | Cheney, II et al. | |
| 6,254,586 | B1 | 7/2001 | Mann et al. | |
| 6,360,888 | B1 | 3/2002 | McIvor et al. | |
| 6,424,847 | B1 * | 7/2002 | Mastrototaro et al. | 600/316 |
| 6,641,533 | B2 | 11/2003 | Causey, III et al. | |
| 6,895,263 | B2 * | 5/2005 | Shin et al. | 600/316 |
| 7,833,157 | B2 * | 11/2010 | Gottlieb et al. | 600/365 |
| 7,972,296 | B2 * | 7/2011 | Braig et al. | 604/66 |
| 2008/0221509 | A1 * | 9/2008 | Gottlieb et al. | 604/43 |

OTHER PUBLICATIONS

Hovorka, et al. "Nonlinear Model Predictive Control of Glucose Concentration in Subjects with Type 1 Diabetes" Institute of Physics Publishing pp. 905-920, 2004.
Van Den Berghe, Greet, et al., "Intensive Insulin Therapy in Critically III Patients" The New England Journal of Medicine, vol. 345, No. 19, Nov. 8, 2001, pp. 1359-1367.
Marchetti, G. et al., "An Improved PID Switching Control Strategy for Type 1 Diabetes", IEEE Transactions on Biomedical Engineering, vol. 35. No. 3, Mar. 1, 2008, pp. 857-863.
Lee, H., et al, "A Closed-Loop Artificial Pancreas Using Model Predictive Control and a Sliding Meal Size Estimator" Journal of Diabetes Science and Technology, vol. 3 No. 5, Sep. 2009, pp. 1082-1090.
PCT/US2011/000284/ 115.P006PCT: PCT application as filed on Feb. 16, 2011, 76 pages.
PCT/US2011/000284/ 115.P006PCT: Initial Publication with International Search Report on Aug. 25, 2011, 77 pages.
PCT/US2011/000284/ 115.P006PCT: International Search Report mailed Jul. 12, 2011, 2 pages.

* cited by examiner

*Primary Examiner* — Theodore Stigell
*Assistant Examiner* — Diva K Chander
(74) *Attorney, Agent, or Firm* — Berkeley Law & Technology Group, LLP

(57) ABSTRACT

Disclosed are methods, systems, etc. for closed-loop glucose control startup. In certain example embodiments, a request for entry of an automatic mode of operation of a glucose monitoring and insulin delivery system for a patient may be detected. An entry of the automatic mode of operation may be controlled based, at least in part, on a detected rate of change of blood glucose concentration of the patient. In certain other example embodiments, initiation of a continual phase of an automatic mode of operation may be controlled based, at least in part, on a time since a most recent manual delivery of a bolus, on a detected rate of change of blood glucose concentration, on a targeted fixed set point, a combination thereof, and so forth.

19 Claims, 19 Drawing Sheets

CLOSED-LOOP GLUCOSE CONTROL STARTUP

BACKGROUND

1. Field

Subject matter disclosed herein relates to monitoring and/or controlling blood glucose levels in patients including, by way of example but not limitation, during a startup period.

2. Information

The pancreas of a normal healthy person produces and releases insulin into the blood stream in response to elevated blood plasma glucose levels. Beta cells (β-cells), which reside in the pancreas, produce and secrete insulin into the blood stream as it is needed. If β-cells become incapacitated or die, a condition known as Type 1 diabetes mellitus (or in some cases, if β-cells produce insufficient quantities of insulin, a condition known as Type 2 diabetes), then insulin may be provided to a body from another source to maintain life or health.

Traditionally, because insulin cannot be taken orally, insulin has been injected with a syringe. More recently, the use of infusion pump therapy has been increasing in a number of medical situations, including for delivering insulin to diabetic individuals. For example, external infusion pumps may be worn on a belt, in a pocket, or the like, and they can deliver insulin into a body via an infusion tube with a percutaneous needle or a cannula placed in subcutaneous tissue.

As of 1995, less than 5% of Type 1 diabetic individuals in the United States were using infusion pump therapy. Presently, over 7% of the more than 900,000 Type 1 diabetic individuals in the U.S. are using infusion pump therapy. The percentage of Type 1 diabetic individuals that use an infusion pump is growing at a rate of over 2% each year. Moreover, the number of Type 2 diabetic individuals is growing at 3% or more per year, and growing numbers of insulin-using Type 2 diabetic individuals are also adopting infusion pumps. Additionally, physicians have recognized that continuous infusion can provide greater control of a diabetic individual's condition, so they too are increasingly prescribing it for patients.

A closed-loop infusion pump system may include an infusion pump that is automatically and/or semi-automatically controlled to infuse insulin into a patient. The infusion of insulin may be controlled to occur at times and in amounts that are based, for example, upon blood glucose measurements obtained from an embedded glucose sensor in real-time. Closed-loop infusion pump systems may also employ the delivery of glucose and/or glucagon, in addition to the delivery of insulin, for controlling blood-glucose levels of a patient (e.g., in a hypoglycemic context).

SUMMARY

Briefly, example embodiments may relate to methods, systems, apparatuses, and/or articles, etc. for closed-loop glucose control startup scenarios.

In one or more example embodiments, a method may include: detecting at a controller a request for entry of an automatic mode of operation of a glucose monitoring and insulin delivery system for a patient; and controlling the entry of the automatic mode of operation based, at least in part, on a detected rate of change of blood glucose concentration of the patient.

In at least one example implementation, the detected rate of change of blood glucose concentration may be based, at least in part, on measurements from one or more glucose sensors.

In at least one other example implementation, the controlling may include delaying initiation of a continual phase of the automatic mode of operation at least until the detected rate of change of blood glucose concentration of the patient is less than a predetermined rate of blood glucose change. In yet at least one other example implementation, the controlling may include delaying initiation of a continual phase of the automatic mode of operation at least until the detected rate of change of blood glucose concentration of the patient indicates that the blood glucose concentration of the patient is not increasing.

In at least one other example implementation, the controlling may include delaying initiation of a continual phase of the automatic mode of operation until at least a predetermined length of time has elapsed since a most-recent manual delivery of a bolus of insulin.

In at least one other example implementation, the controlling may include initiating a continual phase of the automatic mode of operation if a measured blood glucose concentration of the patient does not exceed a target blood glucose concentration for the patient.

In at least one other example implementation, the controlling may include: calculating a correction bolus of insulin based, at least in part, on an insulin-on-board value and a target blood glucose concentration for the patient; and delivering the correction bolus of insulin to the patient if an amount of the correction bolus of insulin exceeds a predetermined minimum bolus amount. In yet at least one other example implementation, the calculating may include calculating the correction bolus of insulin based, at least in part, on the detected rate of change of blood glucose concentration of the patient.

In at least one other example implementation, the controlling may include initiating a continual phase of the automatic mode of operation if the detected rate of change of blood glucose concentration of the patient does not exceed a first predetermined rate of blood glucose change. In yet at least one other example implementation, the controlling may further include: waiting a predetermined period of time if the detected rate of change of blood glucose concentration of the patient exceeds the first predetermined rate of blood glucose change; and after expiration of the predetermined period of time, determining if a correction bolus of insulin is to be delivered based, at least in part, on an insulin-on-board value.

In yet at least one other example implementation, the controlling may further include: comparing the detected rate of change of blood glucose concentration of the patient to a second predetermined rate of blood glucose change if the detected rate of change of blood glucose concentration of the patient exceeds the first predetermined rate of blood glucose change; if the detected rate of change of blood glucose concentration of the patient exceeds the second predetermined rate of blood glucose change, waiting a first predetermined period of time; if the detected rate of change of blood glucose concentration of the patient does not exceed the second predetermined rate of blood glucose change, waiting a second predetermined period of time; and after expiration of the first or second predetermined period of time, determining if a measured blood glucose concentration of the patient exceeds a target blood glucose concentration for the patient.

In at least one other example implementation, the controlling may include: establishing a reference trajectory for a set point of the automatic mode of operation; initiating a continual phase of the automatic mode of operation; and attempting to cause a measured blood glucose concentration of the patient to track the reference trajectory.

In at least one other example implementation, the controlling may include determining a time at which to exit a transitional phase of the automatic mode of operation and enter a continual phase of the automatic mode of operation. In yet at least one other example implementation, the method may further include: providing insulin in accordance with a basal rate and delivering at least one bolus of insulin in accordance with measured blood glucose concentration of the patient during the transitional phase of the automatic mode of operation; and providing insulin in accordance with the current measured blood glucose concentration of the patient during the continual phase of the automatic mode of operation. In still yet at least one other example implementation, the at least one bolus of insulin may be delivered using a relatively discrete mechanism during the transitional phase, and the insulin may be provided using a relatively continual mechanism during the continual phase in accordance with a control algorithm.

In at least one other example implementation, the controlling may include: delaying initiation of a continual phase of the automatic mode of operation until at least a predetermined length of time has elapsed since a most-recent manual delivery of a bolus of insulin; and after at least the predetermined length of time has elapsed, initiating the continual phase of the automatic mode of operation after a measured blood glucose concentration of the patient is less than a target blood glucose concentration for the patient. In yet at least one other example implementation, the controlling may further include: after at least the predetermined length of time has elapsed, initiating the continual phase of the automatic mode of operation after the detected rate of change of blood glucose concentration of the patient becomes less than a predetermined rate of blood glucose change. In still yet at least one other example implementation, the controlling may further include: after at least the predetermined length of time has elapsed, initiating the continual phase of the automatic mode of operation after the detected rate of change of blood glucose concentration of the patient becomes negative.

In at least one other example implementation, the controlling may include delivering at least one of glucose or glucagon to the patient if a measured blood glucose concentration of the patient is less than a threshold glucose concentration level.

In one or more example embodiments, an apparatus may include a controller to receive one or more signals based on glucose sensor measurements. The controller may include one or more processors to: detect a request for entry of an automatic mode of operation of a glucose monitoring and insulin delivery system for a patient; and control the entry of the automatic mode of operation based, at least in part, on a detected rate of change of blood glucose concentration of the patient.

In at least one example implementation, the apparatus may further include: one or more glucose sensors adapted to be coupled to a patient to obtain glucose sensor measurements and adapted to provide the one or more signals based on the glucose sensor measurements, with the detected rate of change of blood glucose concentration being based, at least in part, on measurements obtained from the one or more glucose sensors.

In at least one other example implementation, the controller may be capable of controlling the entry by delaying initiation of a continual phase of the automatic mode of operation at least until the detected rate of change of blood glucose concentration of the patient is less than a predetermined rate of blood glucose change. In yet at least one other example implementation, the controller may be capable of controlling the entry by delaying initiation of a continual phase of the automatic mode of operation at least until the detected rate of change of blood glucose concentration of the patient indicates that the blood glucose concentration of the patient is not increasing.

In at least one other example implementation, the controller may be capable of controlling the entry by delaying initiation of a continual phase of the automatic mode of operation until at least a predetermined length of time has elapsed since a most-recent manual delivery of a bolus of insulin.

In at least one other example implementation, the controller may be capable of controlling the entry by initiating a continual phase of the automatic mode of operation if a measured blood glucose concentration of the patient does not exceed a target blood glucose concentration for the patient.

In at least one other example implementation, the controller may be capable of controlling the entry by: calculating a correction bolus of insulin based, at least in part, on an insulin-on-board value and a target blood glucose concentration for the patient; and delivering the correction bolus of insulin to the patient if an amount of the correction bolus of insulin exceeds a predetermined minimum bolus amount.

In at least one other example implementation, the controller may be capable of calculating the correction bolus of insulin by calculating the correction bolus of insulin based, at least in part, on the detected rate of change of blood glucose concentration of the patient.

In at least one other example implementation, the controller may be capable of controlling the entry by initiating a continual phase of the automatic mode of operation if the detected rate of change of blood glucose concentration of the patient does not exceed a first predetermined rate of blood glucose change. In yet at least one other example implementation, the controller may further be capable of controlling the entry by: waiting a predetermined period of time if the detected rate of change of blood glucose concentration of the patient exceeds the first predetermined rate of blood glucose change; and after expiration of the predetermined period of time, determining if a correction bolus of insulin is to be delivered based, at least in part, on an insulin-on-board value.

In yet at least one other example implementation, the controller may further be capable of controlling the entry by: comparing the detected rate of change of blood glucose concentration of the patient to a second predetermined rate of blood glucose change if the detected rate of change of blood glucose concentration of the patient exceeds the first predetermined rate of blood glucose change; if the detected rate of change of blood glucose concentration of the patient exceeds the second predetermined rate of blood glucose change, waiting a first predetermined period of time; if the detected rate of change of blood glucose concentration of the patient does not exceed the second predetermined rate of blood glucose change, waiting a second predetermined period of time; and after expiration of the first or second predetermined period of time, determining if a measured blood glucose concentration of the patient exceeds a target blood glucose concentration for the patient.

In at least one other example implementation, the controller may be capable of controlling the entry by: establishing a reference trajectory for a set point of the automatic mode of operation; initiating a continual phase of the automatic mode of operation; and attempting to cause a measured blood glucose concentration of the patient to track the reference trajectory.

In at least one other example implementation, the controller may be capable of controlling the entry by determining a time at which to exit a transitional phase of the automatic mode of operation and enter a continual phase of the automatic mode of operation. In yet at least one other example implementation, the one or more processors of the controller may further be to: provide insulin in accordance with a basal rate and deliver at least one bolus of insulin in accordance with measured blood glucose concentration of the patient during the transitional phase of the automatic mode of operation; and provide insulin in accordance with the current measured blood glucose concentration of the patient during the continual phase of the automatic mode of operation. In still yet at least one other example implementation, the at least one bolus of insulin may be delivered using a relatively discrete mechanism during the transitional phase, and the insulin may be provided using a relatively continual mechanism during the continual phase in accordance with a control algorithm.

In at least one other example implementation, the controller may be capable of controlling the entry by: delaying initiation of a continual phase of the automatic mode of operation until at least a predetermined length of time has elapsed since a most-recent manual delivery of a bolus of insulin; and after at least the predetermined length of time has elapsed, initiating the continual phase of the automatic mode of operation after a measured blood glucose concentration of the patient is less than a target blood glucose concentration for the patient. In yet at least one other example implementation, the controller may be capable of controlling the entry by, after at least the predetermined length of time has elapsed, initiating the continual phase of the automatic mode of operation after the detected rate of change of blood glucose concentration of the patient becomes less than a predetermined rate of blood glucose change. In still yet at least one other example implementation, the controller may be capable of controlling the entry by, after at least the predetermined length of time has elapsed, initiating the continual phase of the automatic mode of operation after the detected rate of change of blood glucose concentration of the patient becomes negative.

In at least one other example implementation, the controller may be capable of controlling the entry by delivering at least one of glucose or glucagon to the patient if a measured blood glucose concentration of the patient is less than a threshold glucose concentration level.

In at least one other example implementation, the one or more processors of the controller may further be to: selectively delay initiation of a continual phase of the automatic mode of operation based on a length of time that has elapsed since a most-recent manual delivery of a bolus of insulin; and selectively delay initiation of the continual phase of the automatic mode of operation while a measured blood glucose concentration of the patient is increasing as determined from the detected rate of change of blood glucose concentration of the patient.

In one or more example embodiments, an apparatus may include: means for detecting at a controller a request for entry of an automatic mode of operation of a glucose monitoring and insulin delivery system for a patient; and means for controlling the entry of the automatic mode of operation based, at least in part, on a detected rate of change of blood glucose concentration of the patient.

In at least one example implementation, the means for controlling may include means for delaying initiation of a continual phase of the automatic mode of operation at least until the detected rate of change of blood glucose concentration of the patient is less than a predetermined rate of blood glucose change.

In at least one other example implementation, the means for controlling may include means for delaying initiation of a continual phase of the automatic mode of operation until at least a predetermined length of time has elapsed since a most-recent manual delivery of a bolus of insulin.

In at least one other example implementation, the means for controlling may include means for initiating a continual phase of the automatic mode of operation if a measured blood glucose concentration of the patient does not exceed a target blood glucose concentration for the patient.

In at least one other example implementation, the means for controlling may include means for initiating a continual phase of the automatic mode of operation if the detected rate of change of blood glucose concentration of the patient does not exceed a first predetermined rate of blood glucose change.

In at least one other example implementation, the means for controlling may include: means for establishing a reference trajectory for a set point of the automatic mode of operation; means for initiating a continual phase of the automatic mode of operation; and means for attempting to cause a measured blood glucose concentration of the patient to track the reference trajectory.

In one or more example embodiments, an article may include at least one storage medium having stored thereon instructions executable by one or more processors to: detect at a controller a request for entry of an automatic mode of operation of a glucose monitoring and insulin delivery system for a patient; and control the entry of the automatic mode of operation based, at least in part, on a detected rate of change of blood glucose concentration of the patient.

In at least one example implementation, to control the entry of the automatic mode of operation, the at least one storage medium may have stored thereon further instructions executable by one or more processors to determine a time at which to exit a transitional phase of the automatic mode of operation and enter a continual phase of the automatic mode of operation. In yet at least one other example implementation, the at least one storage medium may have stored thereon further instructions executable by one or more processors to: provide insulin in accordance with a basal rate and deliver at least one bolus of insulin in accordance with measured blood glucose concentration of the patient during the transitional phase of the automatic mode of operation; and provide insulin in accordance with the current measured blood glucose concentration of the patient during the continual phase of the automatic mode of operation. In still yet at least one other example implementation, the at least one bolus of insulin may be delivered using a relatively discrete mechanism during the transitional phase, and the insulin may be provided using a relatively continual mechanism during the continual phase in accordance with a control algorithm.

In at least one other example implementation, to control the entry of the automatic mode of operation, the at least one storage medium may have stored thereon further instructions executable by one or more processors to: delay initiation of a continual phase of the automatic mode of operation until at least a predetermined length of time has elapsed since a most-recent manual delivery of a bolus of insulin; and after at least the predetermined length of time has elapsed, initiate the continual phase of the automatic mode of operation after a measured blood glucose concentration of the patient is less than a target blood glucose concentration for the patient. In yet at least one other example implementation, to control the entry of the automatic mode of operation, the at least one storage medium may have stored thereon further instructions executable by one or more processors to, after at least the predetermined length of time has elapsed, initiate the continual phase of the automatic mode of operation after the detected rate of change of blood glucose concentration of the patient becomes less than a predetermined rate of blood glucose change.

Other alternative example embodiments are described herein and/or illustrated in the accompanying Drawings. Additionally, particular example embodiments may be directed to an article comprising a storage medium including machine-readable instructions stored thereon which, if executed by a special purpose computing device and/or processor, may be directed to enable the special purpose computing device/processor to execute at least a portion of described method(s) according to one or more particular implementations. In other particular example embodiments, a sensor may be adapted to generate one or more signals responsive to a measured blood glucose concentration in a body while a special purpose computing device/processor may be adapted to perform at least a portion of described method(s) according to one or more particular implementations based upon one or more signals generated by the sensor.

BRIEF DESCRIPTION OF THE FIGURES

Non-limiting and non-exhaustive features will be described with reference to the following figures, wherein like reference numerals refer to like parts throughout the various figures.

DETAILED DESCRIPTION

In an example glucose control system environment, blood-glucose measurements may be employed in a closed loop infusion system for regulating a rate of fluid infusion into a body. In particular example embodiments, a control system may be adapted to regulate a rate of insulin, glucagon, and/or glucose infusion into a body of a patient based, at least in part, on a glucose concentration measurement taken from a body (e.g., from a glucose sensor). In certain example implementations, such a system may be designed to model a pancreatic beta cell (β-cell). Here, such a system may control an infusion device to release insulin into a body of a patient in an at least approximately similar concentration profile as might be created by fully functioning human β-cells if such were responding to changes in blood glucose concentrations in the body. Thus, such a closed loop infusion system may simulate a body's natural insulin response to blood glucose levels. Moreover, it may not only make efficient use of insulin, but it may also account for other bodily functions as well because insulin can have both metabolic and mitogenic effects.

According to certain embodiments, examples of closed-loop systems as described herein may be implemented in a hospital environment to monitor and/or control levels of glucose in a patient. Here, as part of a hospital or other medical facility procedure, a caretaker or attendant may be tasked with interacting with a closed-loop system to, for example: enter blood-glucose reference measurements into control equipment to calibrate blood glucose measurements obtained from glucose sensors, make manual adjustments to devices, and/or make changes to therapies, just to name a few examples. Alternatively, according to certain embodiments, examples of closed-loop systems as described herein may be implemented in non-hospital environments to monitor and/or control levels of glucose in a patient. Here, a patient or other non-medical professional may be responsible for interacting with a closed-loop system.

Figure 1:
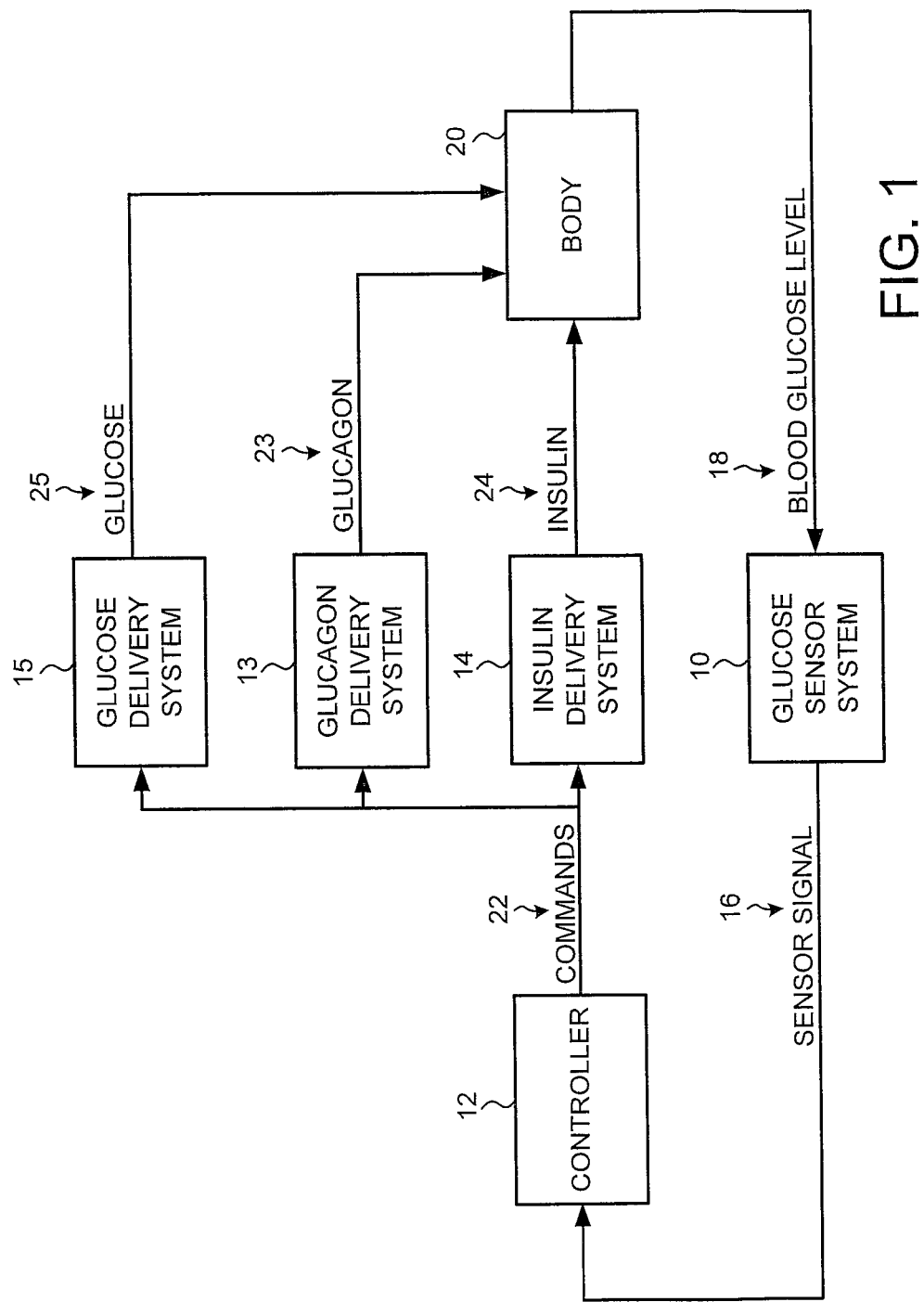
FIG. 1 is a block diagram of an example closed loop glucose control system in accordance with an embodiment.

FIG. 1 is a block diagram of an example closed loop glucose control system in accordance with an embodiment. Particular embodiments may include a glucose sensor system 10, a controller 12, an insulin delivery system 14, a glucagon delivery system 13, and a glucose delivery system 15, as shown in FIG. 1. In certain example embodiments, glucose sensor system 10 may generate a sensor signal 16 representative of blood glucose levels 18 in body 20, and it may provide sensor signal 16 to controller 12. Controller 12 may receive sensor signal 16 and generate commands 22 that are communicated to insulin delivery system 14, glucagon delivery system 13, and/or glucose delivery system 15. Insulin delivery system 14 may receive commands 22 and infuse insulin 24 into body 20 in response to commands 22. Likewise, glucagon delivery system 13 may receive commands 22 and infuse glucagon 23 into body 20 in response to commands 22. Similarly, glucose delivery system 15 may receive commands 22 and infuse glucose 25 into body 20 in response to commands 22.

Glucose sensor system 10 may include a glucose sensor, sensor electrical components to provide power to a sensor and to generate sensor signal 16, a sensor communication system to carry sensor signal 16 to controller 12, and a sensor system housing for electrical components and a sensor communication system. A glucose sensor may measure blood glucose directly from a blood stream, indirectly via interstitial fluid using e.g. a subcutaneous sensor, some combination thereof, and so forth, just to name a few examples. As used herein, "blood glucose", "measured blood glucose", "blood glucose concentration", "measured blood glucose concentration", and the like may refer to a glucose level, a blood glucose level, a blood glucose concentration, and so forth that has been obtained via any type of glucose sensor.

Controller 12 may include electrical components and software to generate commands 22 for insulin delivery system 14, glucagon delivery system 13, and/or glucose delivery system 15 based on sensor signal 16. Controller 12 may also include a controller communication system to receive sensor signal 16 and provide commands 22 to insulin delivery system 14, glucagon delivery system 13, and/or glucose delivery system 15. In particular example implementations, controller 12 may include a user interface and/or operator interface (not shown) comprising a data input device and/or a data output device. Such a data output device may, for example, generate signals to initiate an alarm and/or include a display or printer for showing status of a controller 12 and/or a patient's vital indicators. Such a data input device may comprise dials, buttons, pointing devices, manual switches, alphanumeric keys, a touch-sensitive display, combinations thereof, and/or the like for receiving user and/or operator inputs. It should be understood, however, that these are merely examples of input and output devices that may be a part of an operator and/or user interface and that claimed subject matter is not limited in these respects.

Insulin delivery system 14 may include an infusion device and/or an infusion tube to infuse insulin 24 into body 20. Similarly, glucagon delivery system 13 may include an infusion device and/or an infusion tube to infuse glucagon 23 into body 20. Likewise, glucose delivery system 15 may include an infusion device and/or an infusion tube to infuse glucose 25 into body 20. In alternative embodiments, insulin 24, glucagon 23, and/or glucose 25 may be infused into body 20 using a shared infusion tube. In other alternative embodiments, insulin 24, glucagon 23, and/or glucose 25 may be infused using an intravenous system for providing fluids to a patient (e.g., in a hospital or other medical environment). It should be understood, however, that certain example embodiments may include an insulin delivery system 14 without a glucagon delivery system 13 and/or without a glucose delivery system 15.

In particular embodiments, an infusion device (not explicitly identified in FIG. 1) may include infusion electrical components to activate an infusion motor according to commands 22, an infusion communication system to receive commands 22 from controller 12, and an infusion device housing (not shown) to hold the infusion device.

In particular example embodiments, controller 12 may be housed in an infusion device housing, and an infusion communication system may comprise an electrical trace or a wire that carries commands 22 from controller 12 to an infusion device. In alternative embodiments, controller 12 may be housed in a sensor system housing, and a sensor communication system may comprise an electrical trace or a wire that carries sensor signal 16 from sensor electrical components to controller electrical components. In other alternative embodiments, controller 12 may have its own housing or may be included in a supplemental device. In yet other alternative embodiments, controller 12 may be co-located with an infusion device and a sensor system within a single housing. In further alternative embodiments, a sensor, a controller, and/or infusion communication systems may utilize a cable; a wire; a fiber optic line; RF, IR, or ultrasonic transmitters and receivers; combinations thereof; and/or the like instead of electrical traces, just to name a few examples.

Overview of Example Systems

Figure 2:
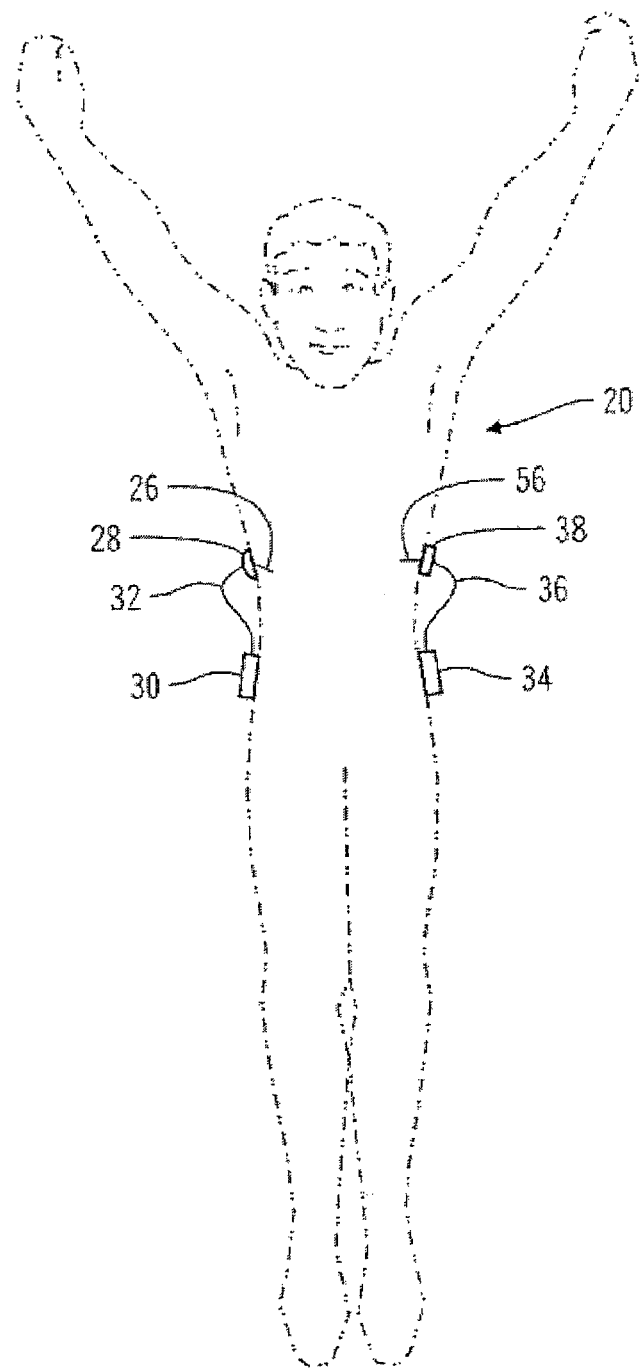
FIG. 2 is a front view of example closed loop hardware located on a body in accordance with an embodiment.
Figure 3:
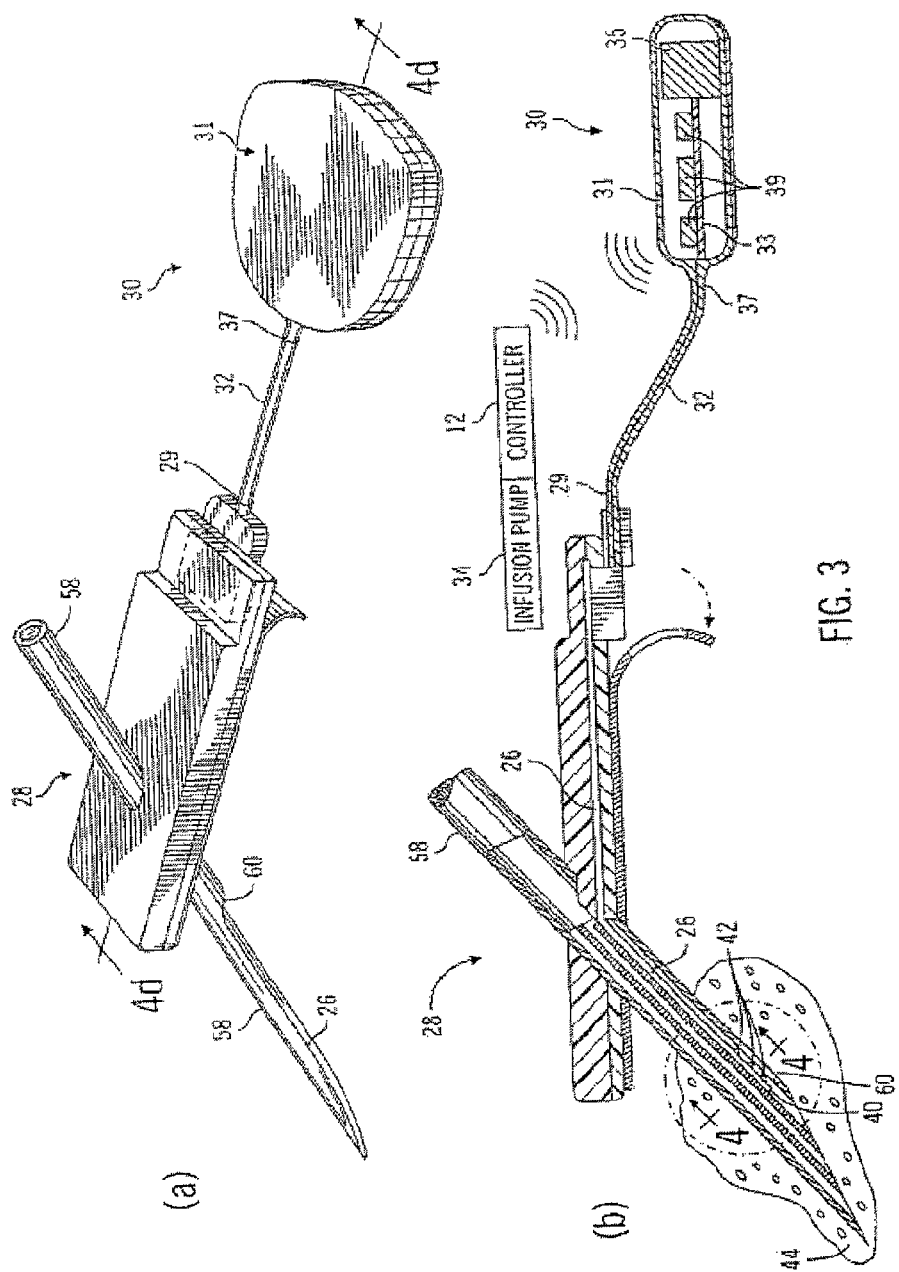
FIG. 3(a) is a perspective view of an example glucose sensor system for use in accordance with an embodiment.
FIG. 3(b) is a side cross-sectional view of a glucose sensor system of FIG. 3(a) for an embodiment.
FIG. 3(c) is a perspective view of an example sensor set of a glucose sensor system of FIG. 3(a) for an embodiment.
FIG. 3(d) is a side cross-sectional view of a sensor set of FIG. 3(c) for an embodiment.
Figure 3:
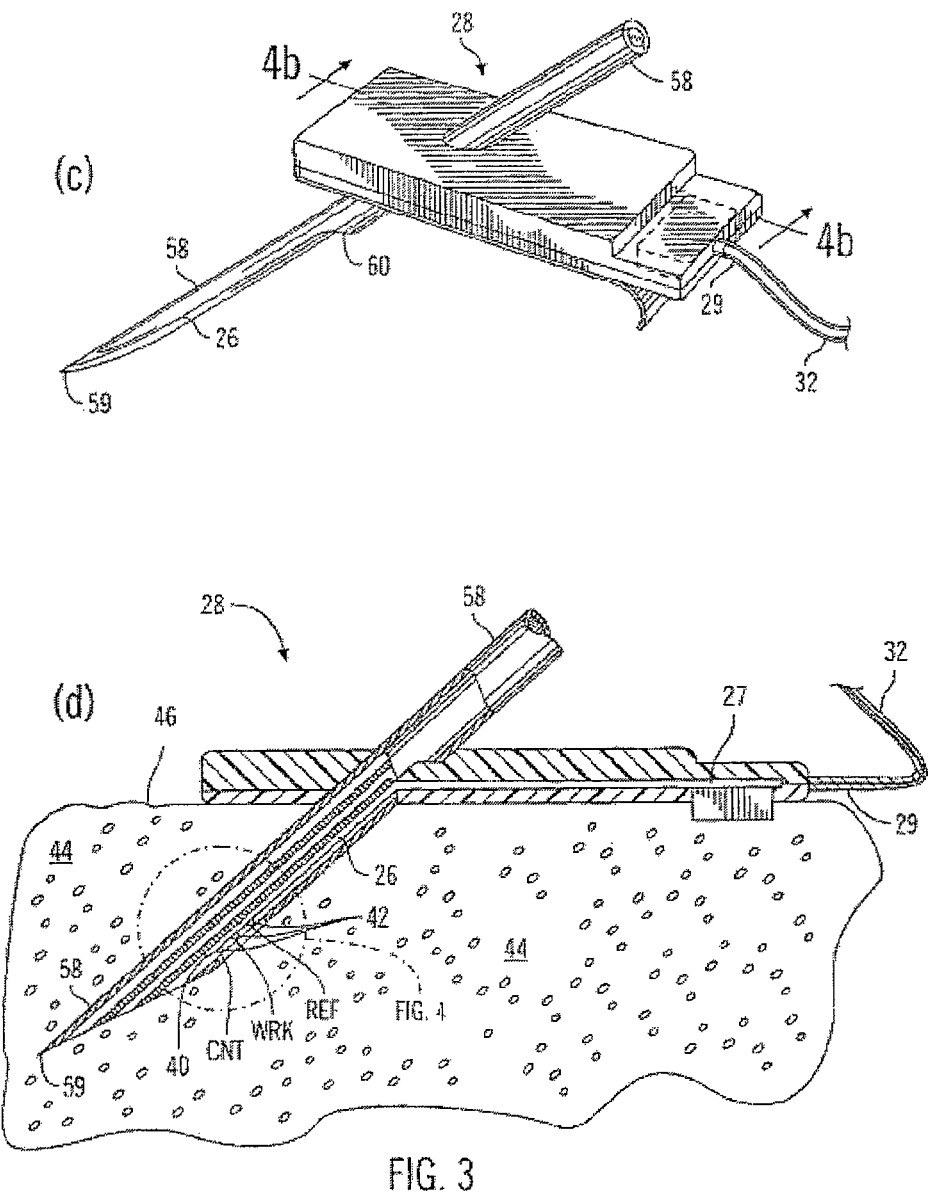
Figure 4:
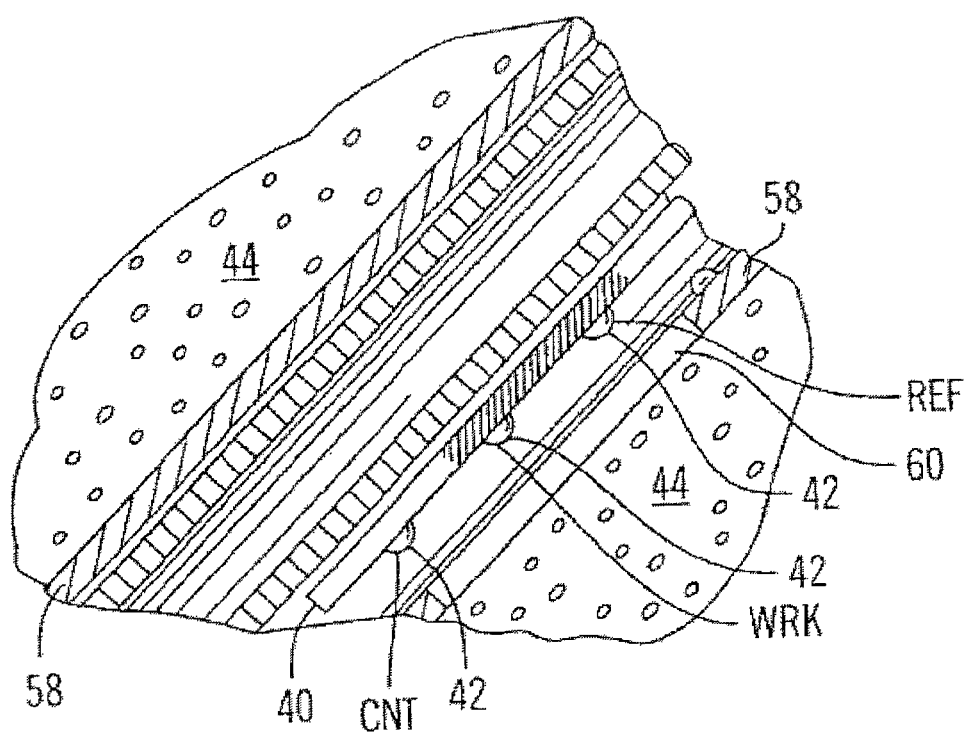
FIG. 4 is a cross sectional view of an example sensing end of a sensor set of FIG. 3(d) for an embodiment.
Figure 5:
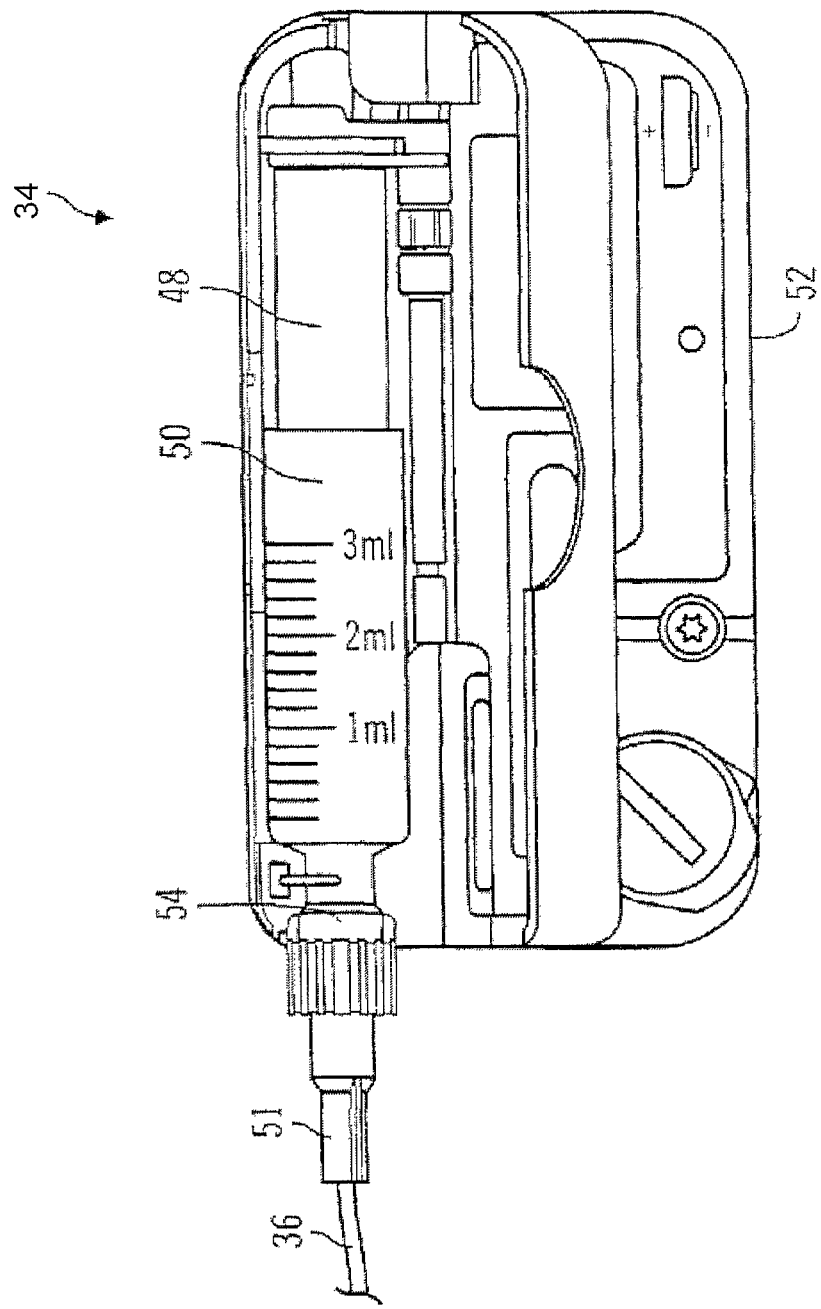
FIG. 5 is a top view of an example infusion device with a reservoir door in an open position, for use according to an embodiment.
Figure 6:
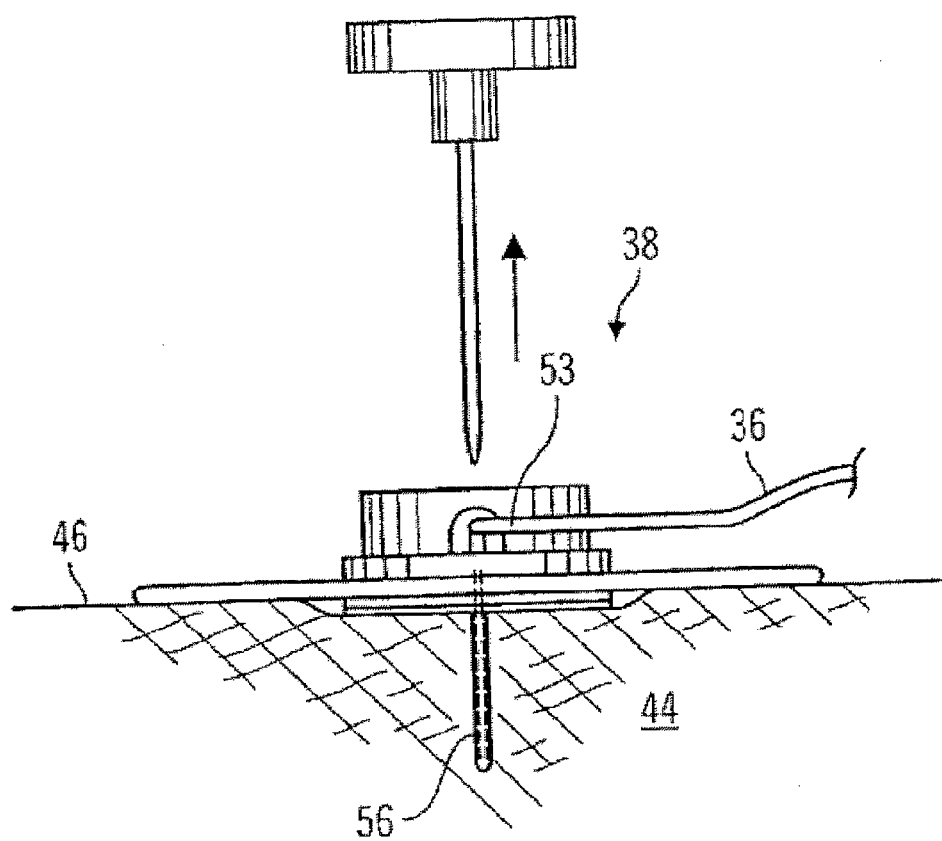
FIG. 6 is a side view of an example infusion set with an insertion needle pulled out, for use according to an embodiment.

FIGS. 2-6 illustrate example glucose control systems in accordance with certain embodiments. FIG. 2 is a front view of example closed loop hardware located on a body in accordance with certain embodiments. FIGS. 3(a)-3(d) and 4 show different views and portions of an example glucose sensor system for use in accordance with certain embodiments. FIG. 5 is a top view of an example infusion device with a reservoir door in an open position in accordance with certain embodiments. FIG. 6 is a side view of an example infusion set with an insertion needle pulled out in accordance with certain embodiments.

Particular example embodiments may include a sensor 26, a sensor set 28, a telemetered characteristic monitor 30, a sensor cable 32, an infusion device 34, an infusion tube 36, and an infusion set 38, any or all of which may be worn on a body 20 of a user or patient, as shown in FIG. 2. As shown in FIGS. 3(a) and 3(b), telemetered characteristic monitor 30 may include a monitor housing 31 that supports a printed circuit board 33, battery or batteries 35, antenna (not shown), a sensor cable connector (not shown), and so forth. A sensing end 40 of sensor 26 may have exposed electrodes 42 that may be inserted through skin 46 into a subcutaneous tissue 44 of a user's body 20, as shown in FIGS. 3(d) and 4. Electrodes 42 may be in contact with interstitial fluid (ISF) that is usually present throughout subcutaneous tissue 44.

Sensor 26 may be held in place by sensor set 28, which may be adhesively secured to a user's skin 46, as shown in FIGS. 3(c) and 3(d). Sensor set 28 may provide for a connector end 27 of sensor 26 to connect to a first end 29 of sensor cable 32. A second end 37 of sensor cable 32 may connect to monitor housing 31. Batteries 35 that may be included in monitor housing 31 provide power for sensor 26 and electrical components 39 on printed circuit board 33. Electrical components 39 may sample sensor signal 16 (e.g., of FIG. 1) and store digital sensor values (Dsig) in a memory. Digital sensor values Dsig may be periodically transmitted from a memory to controller 12, which may be included in an infusion device.

With reference to FIGS. 2 and 5 (and FIG. 1), a controller 12 may process digital sensor values Dsig and generate commands 22 (e.g., of FIG. 1) for infusion device 34. Infusion device 34 may respond to commands 22 and actuate a plunger 48 that forces insulin 24 (e.g., of FIG. 1) out of a reservoir 50 that is located inside an infusion device 34. Glucose may be infused from a reservoir responsive to commands 22 using a similar and/or analogous device (not shown). In alternative implementations, glucose may be administered to a patient orally.

In particular example embodiments, a connector tip 54 of reservoir 50 may extend through infusion device housing 52, and a first end 51 of infusion tube 36 may be attached to connector tip 54. A second end 53 of infusion tube 36 may connect to infusion set 38 (e.g., of FIGS. 2 and 6). With reference to FIG. 6 (and FIG. 1), insulin 24 (e.g., of FIG. 1) may be forced through infusion tube 36 into infusion set 38 and into body 16 (e.g., of FIG. 1). Infusion set 38 may be adhesively attached to a user's skin 46. As part of infusion set 38, a cannula 56 may extend through skin 46 and terminate in subcutaneous tissue 44 to complete fluid communication between a reservoir 50 (e.g., of FIG. 5) and subcutaneous tissue 44 of a user's body 16.

In example alternative embodiments, as pointed out above, a closed-loop system in particular implementations may be a part of a hospital-based glucose management system. Given that insulin therapy during intensive care has been shown to dramatically improve wound healing and reduce blood stream infections, renal failure, and polyneuropathy mortality, irrespective of whether subjects previously had diabetes (See, e.g., Van den Berghe G. et al. NEJM 345: 1359-67, 2001), particular example implementations may be used in a hospital setting to control a blood glucose level of a patient in intensive care. In such alternative embodiments, because an intravenous (IV) hookup may be implanted into a patient's arm while the patient is in an intensive care setting (e.g., ICU), a closed loop glucose control may be established that piggybacks off an existing IV connection. Thus, in a hospital or other medical-facility based system, IV catheters that are directly connected to a patient's vascular system for purposes of quickly delivering IV fluids, may also be used to facilitate blood sampling and direct infusion of substances (e.g., insulin, glucose, anticoagulants, etc.) into an intra-vascular space.

Moreover, glucose sensors may be inserted through an IV line to provide, e.g., real-time glucose levels from the blood stream. Therefore, depending on a type of hospital or other medical-facility based system, such alternative embodiments may not necessarily utilize all of the described system components. Examples of components that may be omitted include, but are not limited to, sensor 26, sensor set 28, telemetered characteristic monitor 30, sensor cable 32, infusion tube 36, infusion set 38, and so forth. Instead, standard blood glucose meters and/or vascular glucose sensors, such as those described in co-pending U.S. Patent Application Publication No. 2008/0221509 (U.S. patent application Ser. No. 12/121,647; to Gottlieb, Rebecca et al.; entitled "MULTILUMEN CATHETER"), filed 15 May 2008, may be used to provide blood glucose values to an infusion pump control, and an existing IV connection may be used to administer insulin to an patient. Other alternative embodiments may also include fewer, more, and/or different components than those that are described herein and/or illustrated in the accompanying Drawings.

Example System and/or Environmental Delays

Example system and/or environmental delays are described herein. Ideally, a sensor and associated component(s) would be capable of providing a real time, noise-free measurement of a parameter, such as a blood glucose measurement, that a control system is intended to control. However, in real-world implementations, there are typically physiological, chemical, electrical, algorithmic, and/or other sources of time delays that cause a sensor measurement to lag behind an actual present value. Also, as noted herein, such a delay may arise from, for instance, a particular level of noise filtering that is applied to a sensor signal.

Figure 7:
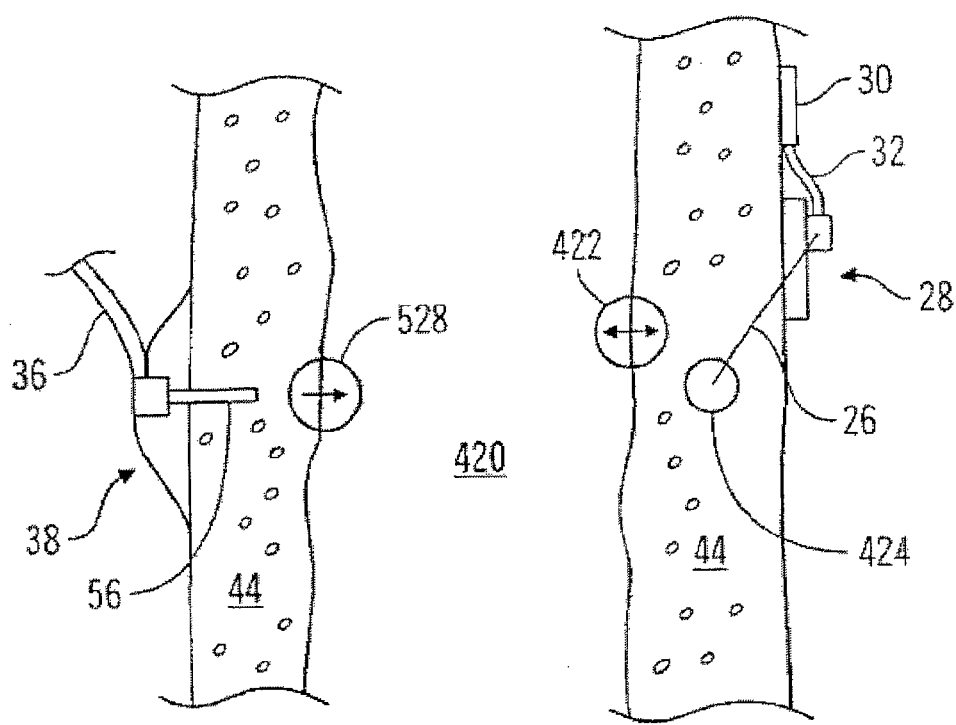
FIG. 7 is a cross-sectional view of an example sensor set and an example infusion set attached to a body in accordance with an embodiment.

FIG. 7 is a cross-sectional view of an example sensor set and an example infusion set that is attached to a body in accordance with an embodiment. In particular example implementations, as shown in FIG. 7, a physiological delay may arise from a time that transpires while glucose moves between blood plasma 420 and interstitial fluid (ISF). This example delay may be represented by a circled double-headed arrow 422. As discussed above with reference to FIG. 2-6, a sensor may be inserted into subcutaneous tissue 44 of body 20 such that electrode(s) 42 (e.g., of FIGS. 3 and 4) near a tip of sensor 40 are in contact with ISF. However, a parameter to be measured may include a concentration of glucose in blood.

Glucose may be carried throughout a body in blood plasma 420. Through a process of diffusion, glucose may move from blood plasma 420 into ISF of subcutaneous tissue 44 and vice versa. As blood glucose level 18 (e.g., of FIG. 1) changes, so does a glucose level of ISF. However, a glucose level of ISF may lag behind blood glucose level 18 due to a time required for a body to achieve glucose concentration equilibrium between blood plasma 420 and ISF. Some studies have shown that glucose lag times between blood plasma and ISF may vary between, e.g., 0 to 30 minutes. Some parameters that may affect such a glucose lag time between blood plasma and ISF are an individual's metabolism, a current blood glucose level, whether a glucose level is rising or falling, combinations thereof, and so forth, just to name a few examples.

A chemical reaction delay 424 may be introduced by sensor response times, as represented by a circle 424 that surrounds a tip of sensor 26 in FIG. 7. Sensor electrodes 42 may be coated with protective membranes that keep electrodes 42 wetted with ISF, attenuate the glucose concentration, and reduce glucose concentration fluctuations on an electrode surface. As glucose levels change, such protective membranes may slow the rate of glucose exchange between ISF and an electrode surface. In addition, there may be chemical reaction delay(s) due to a reaction time for glucose to react with glucose oxidase GOX to generate hydrogen peroxide and a reaction time for a secondary reaction, such as a reduction of hydrogen peroxide to water, oxygen, and free electrons.

Thus, an insulin delivery delay may be caused by a diffusion delay, which may be a time for insulin that has been infused into a tissue to diffuse into the blood stream. Other contributors to insulin delivery delay may include, but are not limited to: a time for a delivery system to deliver insulin to a body after receiving a command to infuse insulin; a time for insulin to spread throughout a circulatory system once it has entered the blood stream; and/or by other mechanical, electrical/electronic, or physiological causes alone or in combination, just to name a few examples. In addition, a body clears insulin even while an insulin dose is being delivered from an insulin delivery system into the body. Because insulin is continuously cleared from blood plasma by a body, an insulin dose that is delivered to blood plasma too slowly or is delayed is at least partially, and possibly significantly, cleared before the entire insulin dose fully reaches blood plasma. Therefore, an insulin concentration profile in blood plasma may never achieve a given peak (nor follow a given profile) that it may have achieved if there were no delay.

Moreover, there may also be a processing delay as an analog sensor signal Isig is converted to digital sensor values Dsig. In particular example embodiments, an analog sensor signal Isig may be integrated over one-minute intervals and converted to a number of counts. Thus, in such a case, an analog-to-digital (A/D) conversion time may result in an average delay of 30 seconds. In particular example embodiments, one-minute values may be averaged into 5-minute values before they are provided to controller 12 (e.g., of FIG. 1). A resulting average delay may be two-and-one-half minutes. In example alternative embodiments, longer or shorter integration times may be used that result in longer or shorter delay times.

In other example embodiments, an analog sensor signal current Isig may be continuously converted to an analog voltage Vsig, and an A/D converter may sample voltage Vsig every 10 seconds. Thus, in such a case, six 10-second values may be pre-filtered and averaged to create a one-minute value. Also, five one-minute values may be filtered and averaged to create a five-minute value that results in an average delay of two-and-one-half minutes. In other alternative embodiments, other sensor signals from other types of sensors may be converted to digital sensor values Dsig as appropriate before transmitting the digital sensor values Dsig to another device. Moreover, other embodiments may use other electrical components, other sampling rates, other conversions, other delay periods, a combination thereof, and so forth.

System Configuration Examples

FIG. 8(a)-8(d) illustrate example diagrams of one or more devices and their components for glucose control systems in accordance with certain embodiments. These FIG. 8(a)-8(d) show exemplary, but not limiting, illustrations of components that may be utilized with certain controller(s) that are described herein above. Various changes in components, layouts of such components, combinations of elements, and so forth may be made without departing from the scope of claimed subject matter.

Before it is provided as an input to controller 12 (e.g., of FIG. 1), a sensor signal 16 may be subjected to signal conditioning such as pre-filtering, filtering, calibrating, and so forth, just to name a few examples. Components such as a pre-filter, one or more filters, a calibrator, controller 12, etc. may be separately partitioned or physically located together (e.g., as shown in FIG. 8(a)), and they may be included with a telemetered characteristic monitor transmitter 30, an infusion device 34, a supplemental device, and so forth.

In particular example embodiments, a pre-filter, filter(s), and a calibrator may be included as part of telemetered characteristic monitor transmitter 30, and a controller (e.g., controller 12) may be included with infusion device 34, as shown in FIG. 8(b). In example alternative embodiments, a pre-filter may be included with telemetered characteristic monitor transmitter 30, and a filter and calibrator may be included with a controller in an infusion device, as shown in FIG. 8(c). In other alternative example embodiments, a pre-filter may be included with telemetered characteristic monitor transmitter 30, while filter(s) and a calibrator are included in supplemental device 41, and a controller may be included in the infusion device, as shown in FIG. 8(d).

In particular example embodiments, a sensor system may generate a message that includes information based on a sensor signal such as digital sensor values, pre-filtered digital sensor values, filtered digital sensor values, calibrated digital sensor values, commands, and so forth, just to name a few examples. Such a message may include other types of information as well, including, by way of example but not limitation, a serial number, an ID code, a check value, values for other sensed parameters, diagnostic signals, other signals, and so forth. In particular example embodiments, digital sensor values Dsig may be filtered in a telemetered characteristic monitor transmitter 30, and filtered digital sensor values may be included in a message sent to infusion device 34 where the filtered digital sensor values may be calibrated and used in a controller. In other example embodiments, digital sensor values Dsig may be filtered and calibrated before transmission to a controller in infusion device 34. Alternatively, digital sensor values Dsig may be filtered, calibrated, and used in a controller to generate commands 22 that are sent from telemetered characteristic monitor transmitter 30 to infusion device 34.

Figure 8:
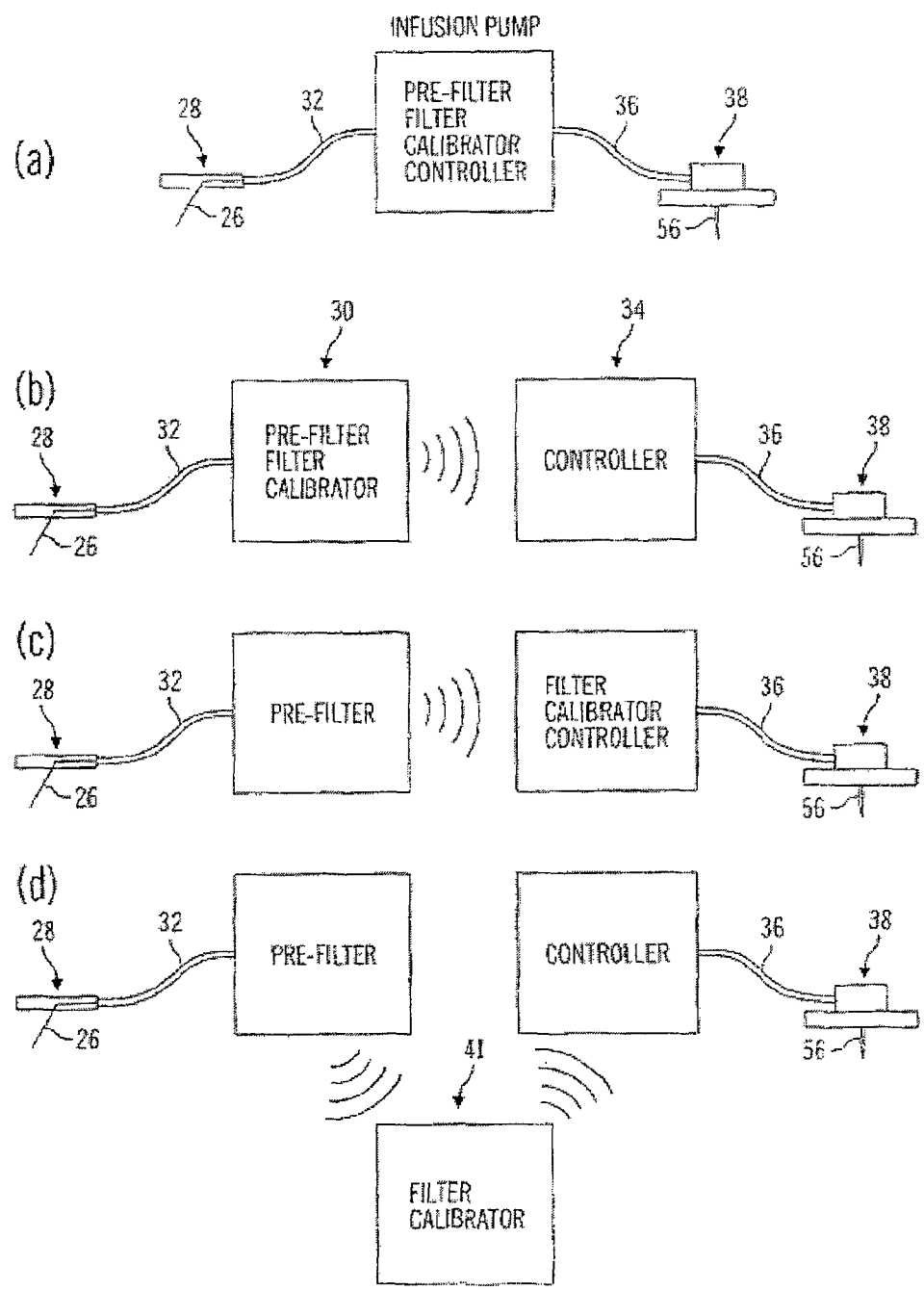
FIG. 8(a) is a diagram of an example single device and its components for a glucose control system in accordance with an embodiment.
FIG. 8(b) is a diagram of two example devices and their components for a glucose control system in accordance with an embodiment.
FIG. 8(c) is another diagram of two example devices and their components for a glucose control system in accordance with an embodiment.
FIG. 8(d) is a diagram of three example devices and their components for a glucose control system in accordance with an embodiment.

In further example embodiments, additional components, such as a post-calibration filter, a display, a recorder, a blood glucose meter, etc. may be included in devices with any of the other components, or they may stand-alone. If a blood glucose meter is built into a device, for instance, it may be co-located in the same device that contains a calibrator. In alternative example embodiments, more, fewer, and/or different components may be implemented than those that are shown in FIG. 8 and/or described herein above.

In particular example embodiments, RF telemetry may be used to communicate between devices that contain one or more components, such as telemetered characteristic monitor transmitter 30 and infusion device 34. In alternative example embodiments, other communication mediums may be employed between devices, such as wires, cables, IR signals, laser signals, fiber optics, ultrasonic signals, and so forth, just to name a few examples.

Example Modes of Operation

Closed-loop regulation of blood glucose may differ from typical control problems in a number of respects, and a start up procedure is an example of one. For most situations when a control system is engaged, there is little that a human operator can do to significantly influence performance of the closed-loop system during an initial period of operation. In contrast, with blood glucose regulation an individual can take actions (e.g., such as giving a correction bolus of insulin shortly before engaging a closed-loop system) that can have significant effects. These significant effects can reach a point of increasing the risk of adverse events such as severe hypoglycemia. Consequently, startup strategies that extend beyond a conventional-transfer approach may be implemented to address and at least partially remedy one or more of such significant, potentially deleterious, effects. Described herein are example embodiments of startup algorithms that may be used, for example, in the context of glycemic regulation. Although particular example implementations describe proportional-integral-derivative (PID) control algorithm strategies for use in conjunction with startup algorithms, claimed subject matter is not so limited, for startup algorithms may be implemented with other control strategy or strategies.

Figure 9:
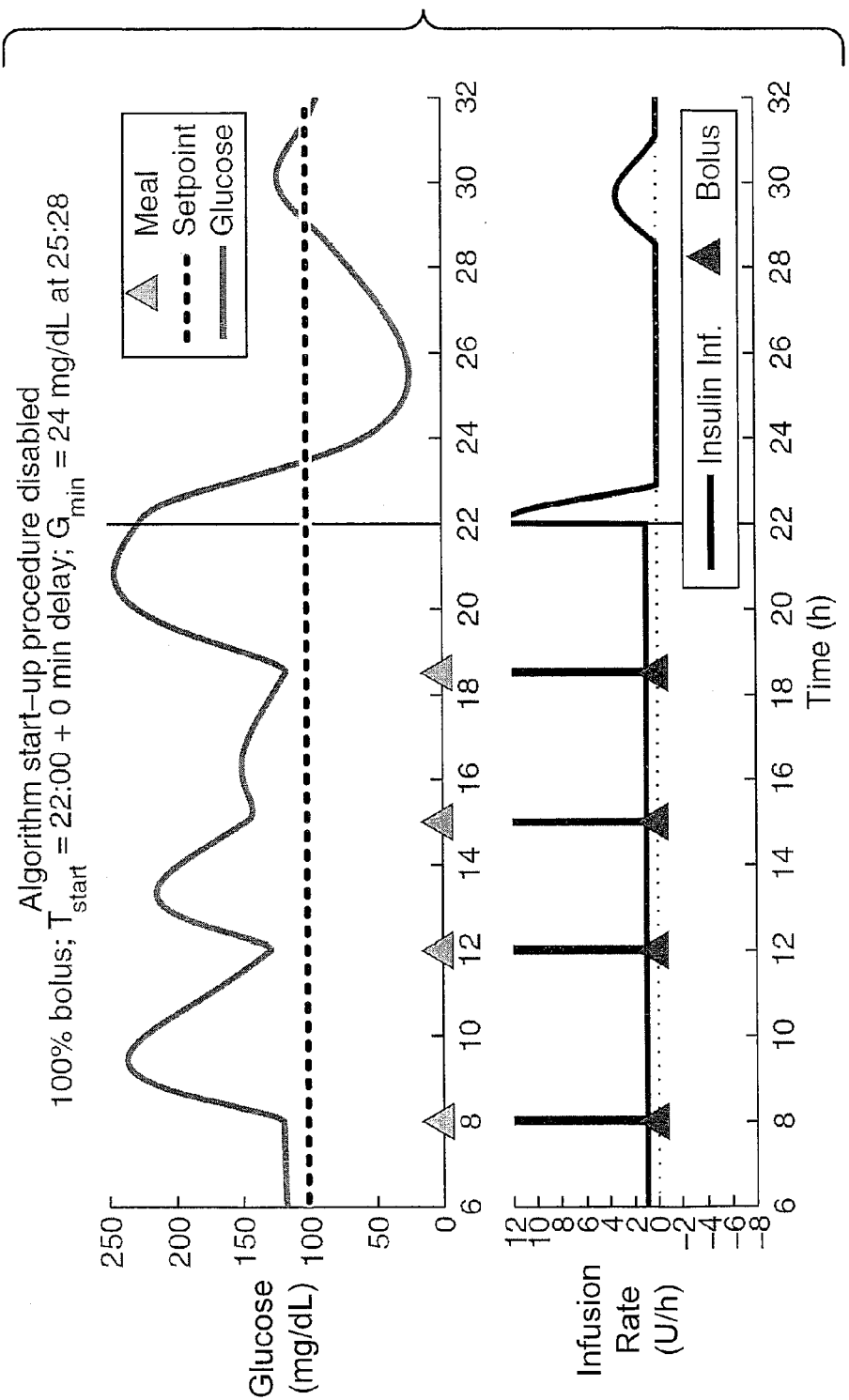
FIG. 9 illustrates two graphs that depict an activation of close-loop control with an example conventional transfer transition.

FIG. 9 illustrates two graphs at 901 that depict an activation of close-loop control with an example conventional transfer transition. Abscissa axes for both graphs represent time in hours from 6 to 32. An ordinate axis for the upper graph represents glucose (mg/dL), and an ordinate axis for the lower graph represents an infusion rate (U/h). The graphs jointly depict results for an example simulation for activation of close-loop control at 22 hours, as indicated by the vertical line at 22 hours.

In the upper graph, triangles represent meals, the solid line represents a current glucose level, and the dotted line represents a desired or targeted glucose level. In the lower graph, triangles represent boluses of insulin, and the solid line represents insulin being supplied to a body by way of infusion.

More specifically, an example simulation as illustrated in graphs 901 of FIG. 9 entails a start of closed-loop control at 22:00 h after a 90 g carbohydrate and high fat meal at 18:30. A full manual bolus is supplied with the meal at 18:30 as indicated by the right-most triangle in the upper graph. A conventional transfer strategy is used to initialize a controller as it enters closed-loop control at 22:00 h. With a conventional transfer strategy as reflected in the illustrated simulation, there is a severe hypoglycemic event starting at 10 minutes past midnight (10 minutes past 24:00 h). This is indicated by the solid line in the upper graph as blood glucose falls below 50 mg/dL. If untreated, this severe hypoglycemic event reaches a nadir of 24 mg/dL 80 minutes later (at 25:30 h), even though the control algorithm with a conventional transfer strategy ceases the infusion of insulin a few minutes before 23:00 h.

Figure 10:
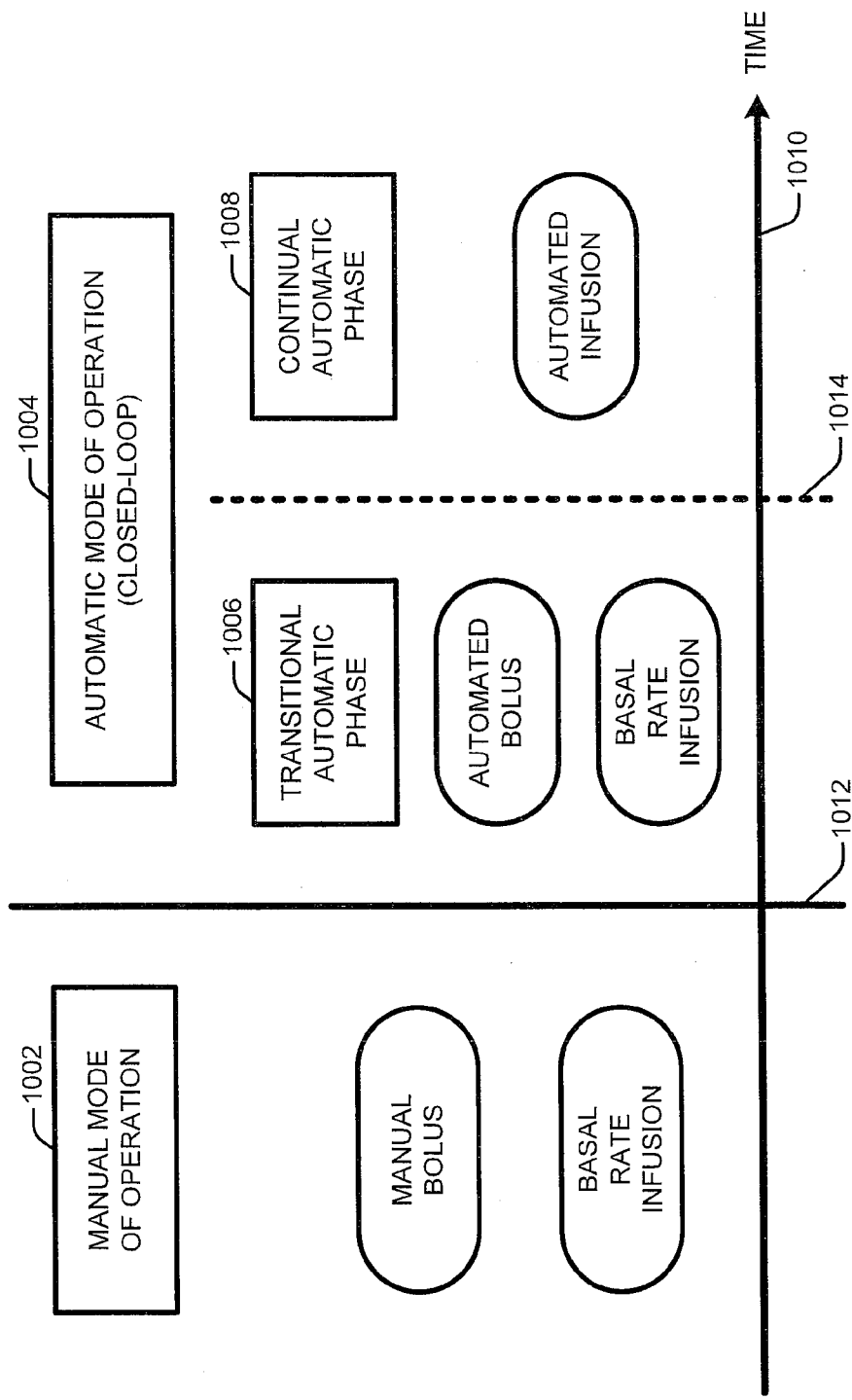
FIG. 10 is a block diagram illustrating characteristics of two different modes of operation, manual and automatic, with an example automatic mode including a transitional phase and a continual phase in accordance with an embodiment.

FIG. 10 is a block diagram 1000 illustrating characteristics of two different modes of operation, manual and automatic, with an example automatic mode including a transitional phase and a continual phase in accordance with an embodiment. As illustrated, block diagram 1000 includes an example manual mode of operation 1002 and an example automatic mode of operation 1004. In particular example embodiments, automatic mode of operation 1004 may correspond to a closed-loop form of operation. Automatic mode of operation 1004 may include an example transitional automatic phase 1006 and/or an example continual automatic phase 1008.

As illustrated, block diagram 1000 also includes a time axis 1010 and two vertical lines of demarcation 1012 and 1014. Line 1012 indicates a user's request for entry of automatic mode of operation 1004. Line 1014 indicates when automatic mode of operation 1004 switches from transitional automatic phase 1006 to continual automatic phase 1008.

In certain example embodiments, insulin may be supplied to a body differently in manual mode of operation 1002 as compared to automatic mode of operation 1004. Insulin may be supplied to a body using a manual bolus and/or using basal rate infusion during manual mode of operation 1002. During automatic mode of operation 1004, insulin may be supplied to a body differently depending on a particular phase that is currently active or in effect. With transitional automatic phase 1006, insulin may be supplied to a body using an automated bolus and/or using basal rate infusion. With continual automatic phase 1008, insulin may be supplied to a body using automated infusion (e.g., without boluses).

In an example manual mode of operation 1002, a device may infuse insulin at a rate sufficient to meet basal needs of a patient. This infusion may be implemented by supplying insulin at, e.g., regular intervals using an insulin pump. If a user determines that additional insulin beyond a basal rate is advisable (e.g., because carbohydrates are being consumed), the user may instruct a device to deliver a manual bolus using, e.g., a relatively discrete mechanism. A bolus may comprise a relatively discrete amount of insulin that is supplied to a patient; however, a given device may actually utilize multiple pumps (e.g., strokes) of an insulin pump (e.g., over multiple seconds, minutes, etc.) to supply a single "discrete" bolus. For instance, an insulin pump may be designed to provide a fixed amount of insulin upon each pumping action, so multiple such pumping actions may be used to total a given bolus amount.

In an example automatic mode of operation 1004, a basal rate infusion of insulin may be continued during a transitional automatic phase 1006. Insulin may be infused using a relatively continual mechanism that supplies insulin, e.g., at regular intervals, at a predetermined amount over a predetermined period of time, and so forth, just to name a few examples. Additionally, a device may determine whether an automated bolus should be delivered based on one or more measurements of blood glucose concentration of a patient. Such an automated correction bolus may be delivered using a relatively discrete mechanism.

In particular example embodiments, a device can determine if, when, and/or how to switch from transitional automatic phase 1006 to continual automatic phase 1008 based, at least in part, on one or more factors, one or more blood glucose concentration measurements, changes (or rate of change) to blood glucose concentrations, and so forth, just to name a few examples. During continual automatic phase 1008, infusion of insulin may be automated in accordance with a control algorithm. A set point for a control algorithm may be fixed, changing, matched to a reference trajectory (e.g., a desired transition path towards a fixed value), some combination thereof, and so forth, just to name a few examples. Automated infusion may be accomplished using, for example, a relatively continual mechanism in conjunction with a control algorithm. A control algorithm may be a proportional-integral-derivative (PID) control algorithm or another algorithm type. Example implementations for these and other embodiments are described further herein below. However, claimed subject matter is not limited to the description above or the examples below.

In example general situations, initiating closed-loop control of glycemia may present challenges given that a patient may take a variety of action(s) that can have a significant impact on performance. In some cases, such action(s) can result in potentially harmful or dangerous conditions for a patient. Certain example embodiments for start-up algorithms that are described herein address one or more of these different possible actions so as to take them into consideration and possibly account for them. Certain example algorithms may further incorporate proactive actions and/or appropriate responses in order to improve overall performance in a safe manner.

A number of example aspects may be considered for a startup algorithm. Two are noted here by way of example but not limitation: (1) Prior knowledge (e.g., insulin-on-board (IOB) and/or current basal rate) may be incorporated into a start-up algorithm; and (2) Initial proactive action, such as delivering an automated bolus, may be taken. One, both, and/or other aspects may be implemented so as to increase performance and/or reduce variability.

With respect to incorporating prior knowledge, a startup algorithm may be initialized with regard to a then-current basal rate. However, this may be related to a conventional transfer approach, which can be used in control systems generally. Prior insulin delivery may be alternatively and/or further incorporated by using an IOB concept. IOB may refer to bolus delivery or both basal rate and bolus components.

With respect to taking proactive action, upon starting closed-loop control, a correction bolus may be calculated based on a patient's correction factor (e.g., an insulin sensitivity factor (ISF)). By delivering such an automated bolus, a patient's glucose level may converge to a desired target level relatively faster. In combination with an automated correction bolus, a reference trajectory may initially be used for a set point of a control algorithm. Implementing a reference trajectory that aims for a relatively fixed blood glucose concentration level may reduce a possibility of over infusion of insulin during a transitional period from a manual mode of operation, or an open-loop control, to an automatic mode of operation, or a closed-loop control.

It should be understood that aspects described above are examples only and that embodiments may differ there from without departing from claimed subject matter. Also, although FIG. 11, which is described below, illustrates an example application of certain embodiments of a startup algorithm in which a PID control algorithm is implemented, other control algorithm(s) may alternatively be implemented.

Figure 11:
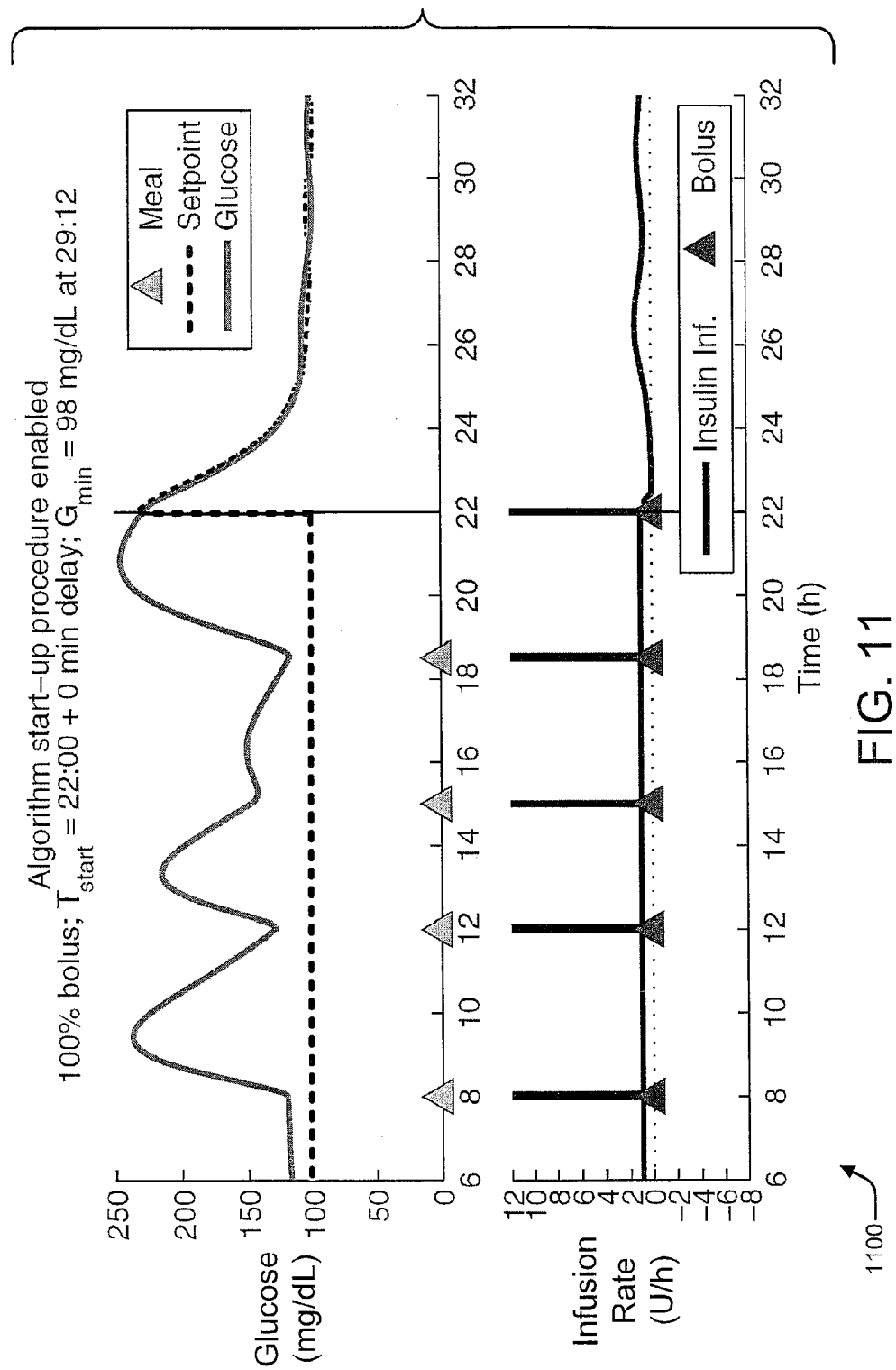
FIG. 11 illustrates two graphs that depict an activation of close-loop control in conjunction with an example start-up scenario that include two phases in accordance with an embodiment.

FIG. 11 illustrates two graphs at 1100 that depict an activation of close-loop control with an example start-up scenario that include two phases in accordance with an embodiment. Graphs 1100 jointly depict results for an example simulation when close-loop control is activated at 22:00 hours, as indicated by the vertical line thereat. Abscissa axes for both graphs represent time in hours from 6 to 32. An ordinate axis for the upper graph represents glucose (mg/dL), and an ordinate axis for the lower graph represents an infusion rate (U/h). In the upper graph, triangles represent meals, the solid line represents a current glucose level, and the dotted line represents a desired or targeted glucose level. In the lower graph, triangles represent boluses of insulin, and the solid line represents insulin being supplied to a body by way of infusion.

More specifically for this example simulation, entry of an automatic mode of operation is requested at 22:00 h after a 90 g carbohydrate and high fat meal at 18:30 h. A full manual bolus is supplied with the meal at 18:30 h. In this example, measured blood glucose concentration, as indicated by the solid line in the upper graph, is decreasing when a user requests entry into an automatic mode of operation. Nevertheless, although blood glucose concentration is decreasing, it is still above a desired fixed set point or targeted level/point. This set point or targeted level is represented by the dotted line in the upper graph. As is apparent from the left side of the upper graph, this dotted line is located at 100 mg/dL. A closed-loop system may facilitate a reduction of blood glucose concentration from a current elevated level down to the set point. As shown by the dotted line on the right side of the upper graph, this reduction may follow a desired reference trajectory.

In this example simulation, whether an automated bolus is appropriate is calculated as part of a transitional automatic phase at or after 22:00 hours, when a request for entry to an automatic mode of operation is made. In this simulated case, an automated correction bolus is indicated based on a current measured blood glucose concentration of over 200 mg/dL. Consequently, an automated bolus is delivered by a device, as indicated by the right-most triangle in the lower graph at 22:00 hours. Because measured blood glucose concentration is decreasing at 22:00 hours, a continual automatic phase may be activated. In contrast with the upper graph of FIG. 9, hypoglycemia is avoided as shown by the solid line in the upper graph of FIG. 11.

To further smooth overall entry into an automatic mode of operation, a current (but changing) set point may be established to be a falling reference trajectory that targets a desired relatively fixed set point (e.g., 100 mg/dL in FIG. 11). An example falling trajectory may be established as shown by the dotted line of the upper graph. Measured blood glucose concentration may track such a falling trajectory as shown by the overlapping solid line. Matching a targeted set point to a reference trajectory may be implemented during, e.g., a relatively earlier portion of a continual phase of an automatic mode of operation. Although a falling reference trajectory is shown in FIG. 11 and described above, a reference trajectory that is initially rising may alternatively be implemented. Example embodiments relating to an initially-rising reference trajectory are described further herein below with particular reference to FIG. 17.

In example alternative embodiments, initiation of a continual automatic phase may be delayed a predetermined time period since a previous administration of a manual bolus. In other example alternative embodiments, if a measured blood glucose concentration of a patient is rising, initiation of a continual automatic phase may be delayed for one or more predetermined time periods. Still other alternative embodiments may be implemented without departing from claimed subject matter.

Figure 12:
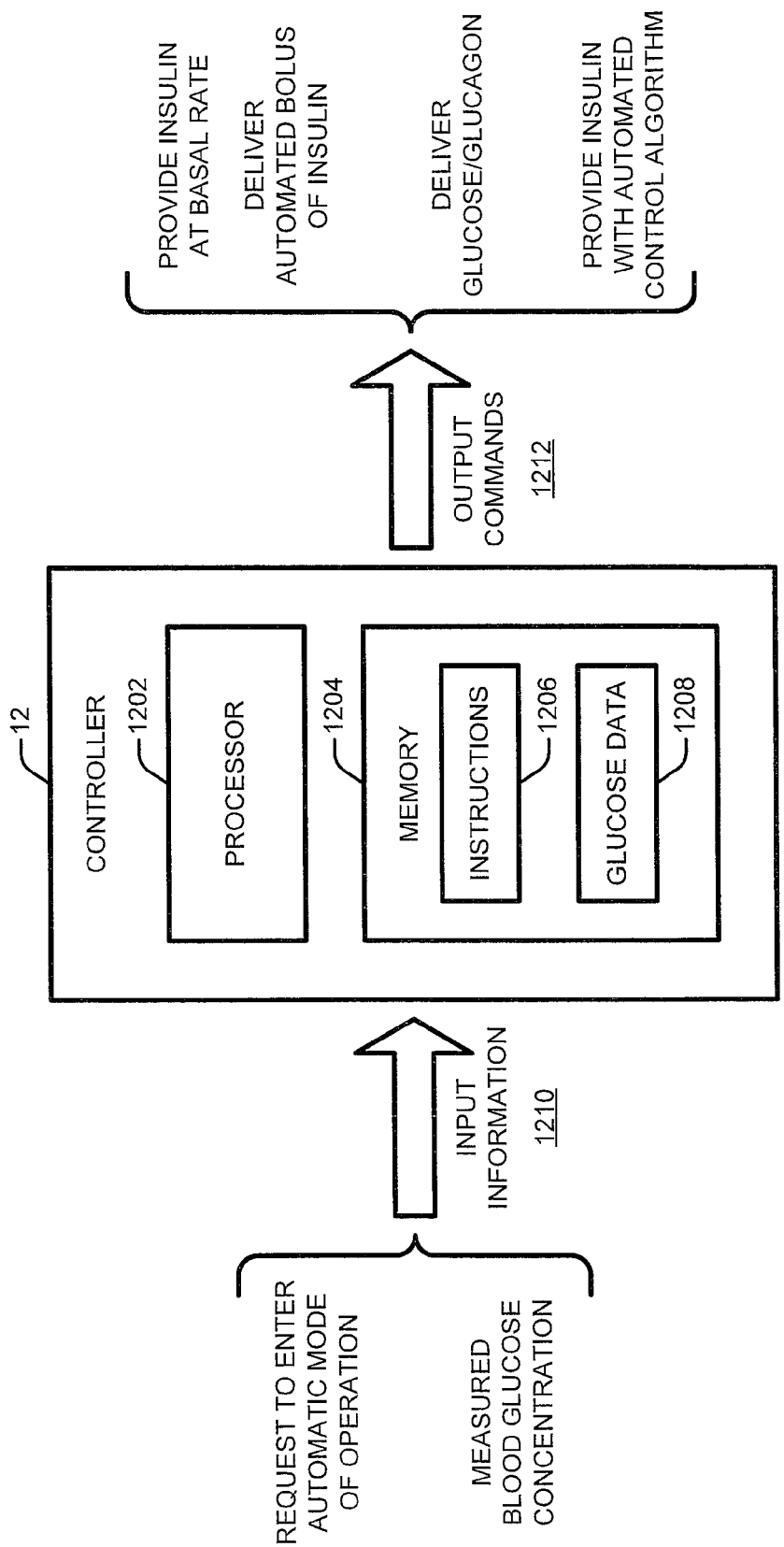
FIG. 12 is a block diagram of an example controller that produces output commands based on input information in accordance with an embodiment.

FIG. 12 is a block diagram of an example controller 12 that produces output commands 1212 based on input information 1210 in accordance with an embodiment. As illustrated, controller 12 may include one or more processors 1202 and at least one memory 1204. In certain example embodiments, memory 1204 may store or otherwise include instructions 1206 and/or glucose data 1208. Glucose data 1208 may include, by way of example but not limitation, reference glucose values, measured blood glucose concentration values, times and/or amounts of glucose bolus administrations, insulin on board (IOB), basal rate, combinations thereof, and so forth. Input information 1210 may include at least one request to enter an automatic mode of operation, one or more measured blood glucose concentration values/signals, and so forth, just to name a few examples. Output commands 1212 may include: provide insulin at basal rate, deliver automated bolus of insulin, deliver glucose and/or glucagon, provide insulin with automated control algorithm, and so forth, just to name a few examples.

Figure 16:
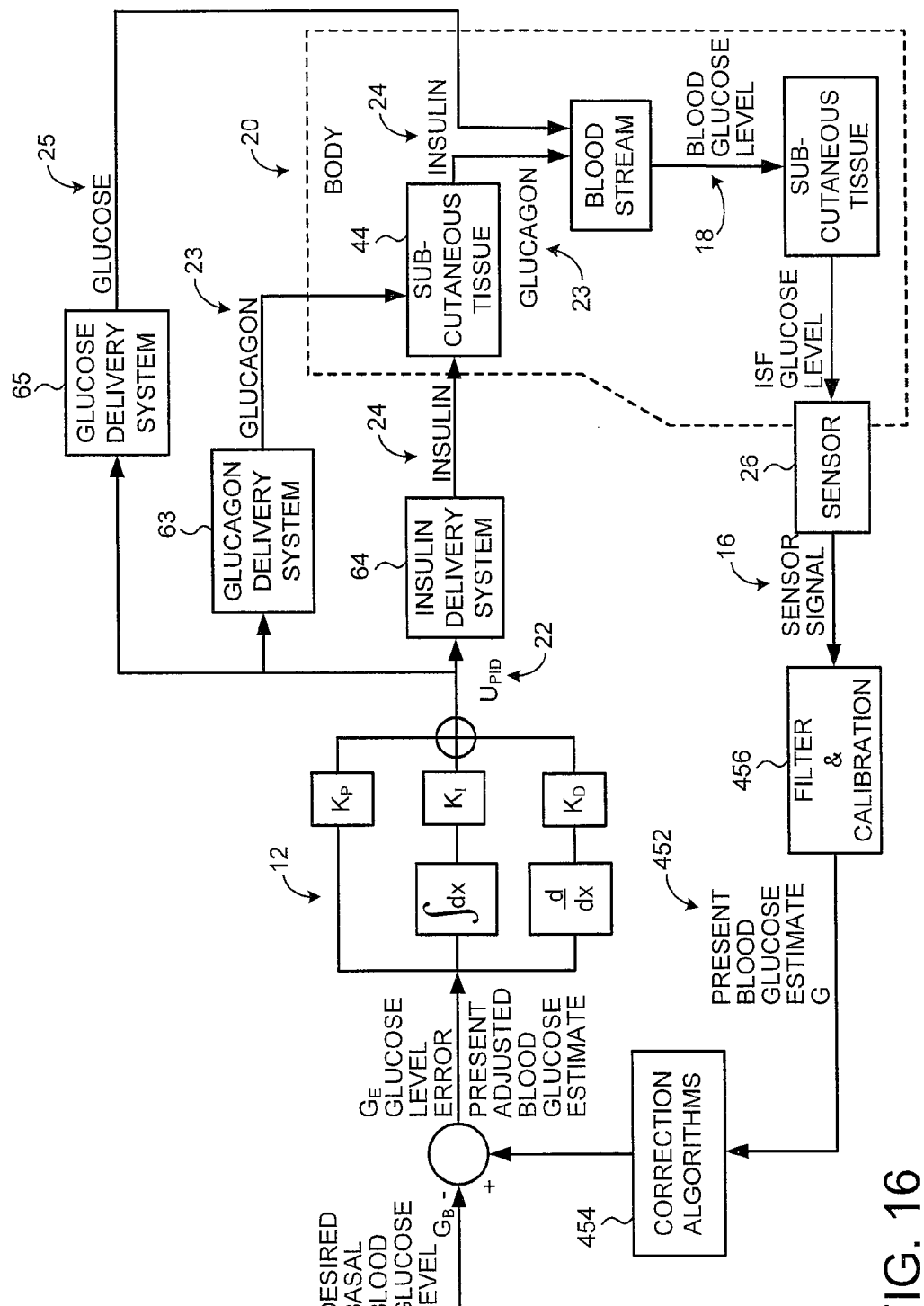
FIG. 16 is a block diagram of an example closed loop system to control blood glucose levels using a proportional-integral-derivative (PID) control algorithm through insulin infusion based on glucose level feedback in accordance with an embodiment.

In particular example implementations, controller 12 of FIG. 12 may correspond to controller 12 of FIG. 1, 16, and so forth. Measured blood glucose concentrations of input information 1210 may correspond to sensor signal 16 (e.g., of FIGS. 1 and 16) and/or values resulting there from. Output commands 1212 may correspond to commands 22 (e.g., of FIGS. 1 and 16) and/or values derived there from.

In certain example embodiments, input information 1210 may be provided to controller 12. Based on input information 1210, controller 12 may produce one or more output commands 1212. Measured blood glucose concentrations that are received as input information 1210 may be stored as blood glucose data 1208.

Controller 12 may be programmed with instructions 1206 to perform algorithms, functions, methods, etc.; to implement attributes, features, etc.; and so forth that are described herein. Controller 12 may therefore be coupled to at least one glucose sensor to receive one or more signals based on glucose sensor measurements. A controller 12 that comprises one or more processors 1202 may execute instructions 1206 to thereby render the controller a special purpose computing device to perform algorithms, functions, methods, etc.; to implement attributes, features, etc.; and so forth that are described herein. Alternatively, an article may comprise at least one storage medium (e.g., such as memory) having stored thereon instructions 1206 that are executable by one or more processors.

Figure 13:
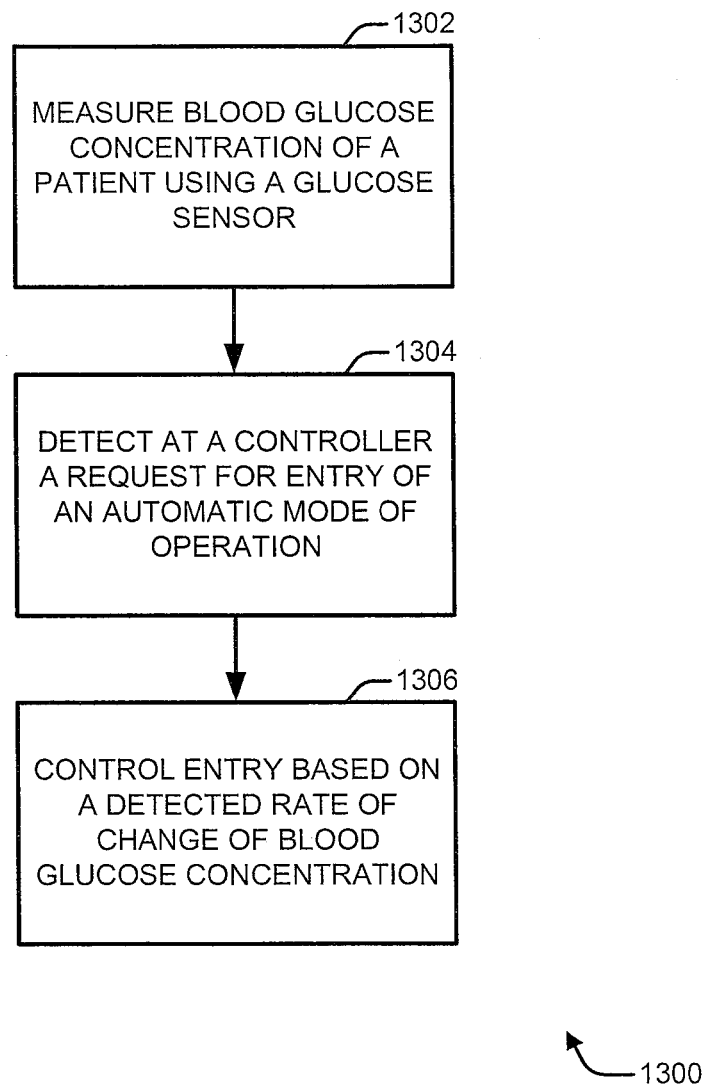
FIG. 13 is a flow diagram of an example method for closed-loop glucose control startup in accordance with an embodiment.

FIG. 13 is a flow diagram 1300 of an example method for closed-loop glucose control startup in accordance with an embodiment. As illustrated, flow diagram 1300 includes three operations 1302-1306. For certain example embodiments, at operation 1302, blood glucose concentration of a patient may be measured by one or more glucose sensors. From multiple (e.g., two or more) blood glucose concentrations that have been measured, a rate of change of blood glucose concentration may be detected.

At operation 1304, a request for entry of an automatic mode of operation of a glucose monitoring and insulin delivery system for a patient may be detected at a controller. At operation 1306, entry of the automatic mode of operation may be controlled based, at least in part, on a detected rate of change of blood glucose concentration of the patient. Although a certain number of operations are specifically illustrated in each flow diagram that is described herein, other embodiments may have a different number and/or different operations without departing from claimed subject matter.

Figure 14:
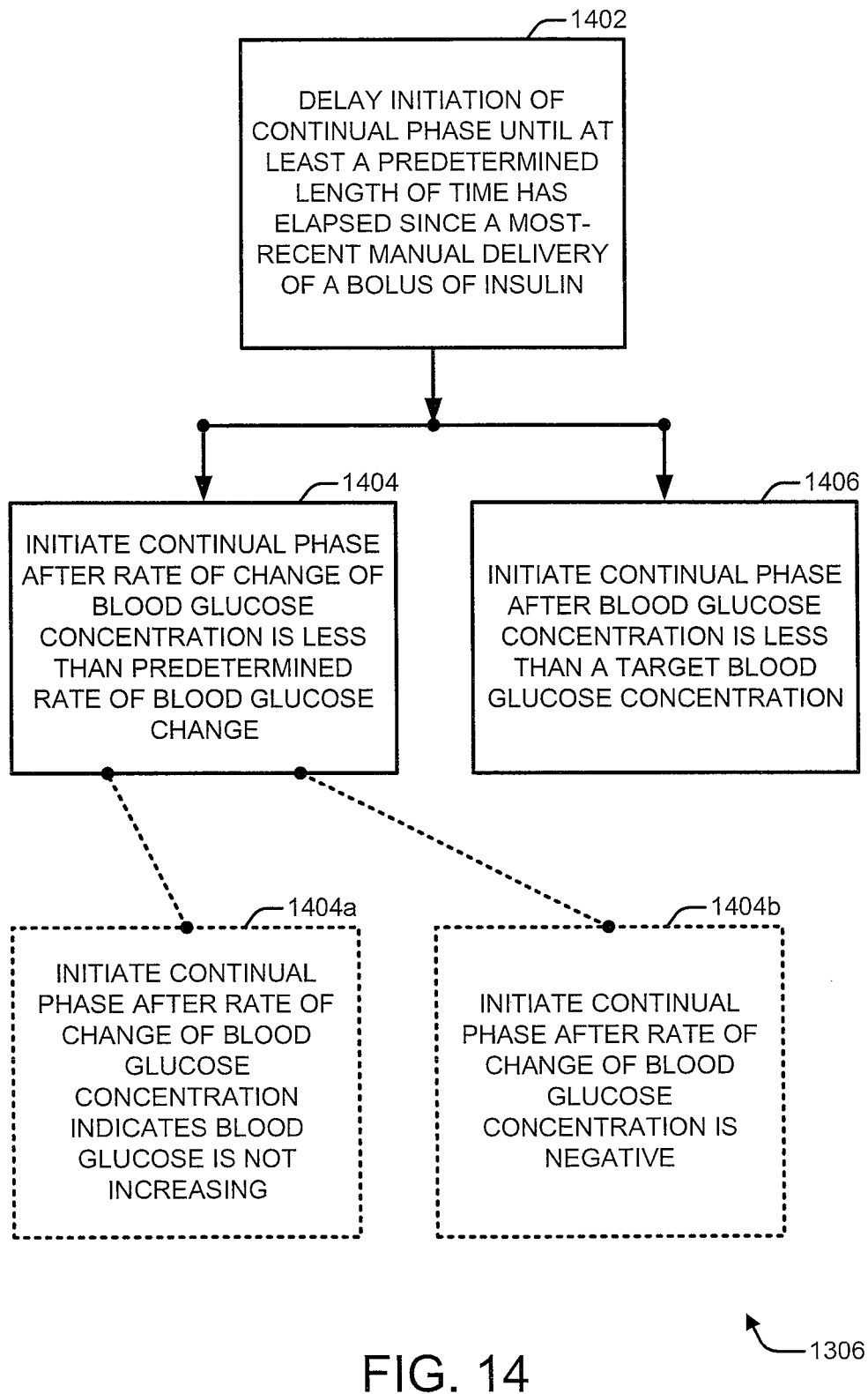
FIG. 14 is a flow diagram of an example method for controlling entry into an automatic mode of operation based on a detected rate of change of blood glucose concentration in accordance with an embodiment.

FIG. 14 is a flow diagram 1306 of an example method for controlling entry into an automatic mode of operation based, at least in part, on a detected rate of change of blood glucose concentration in accordance with an embodiment. As illustrated, flow diagram 1400 includes three operations 1402-1406, plus operations 1404a and 1404b. For certain example embodiments, at operation 1402, initiation of a continual phase of an automatic mode of operation may be delayed until at least a predetermined length of time has elapsed since a most-recent manual delivery of a bolus of insulin. At operation 1404, a continual phase of an automatic mode of operation may be initiated after/when a rate of change of blood glucose concentration for a patient becomes less than a predetermined rate of blood glucose change. In other words, initiation of a continual phase may be delayed at least until a rate of change of blood glucose concentration is less than a predetermined rate of blood glucose change. Alternatively, at operation 1406, a continual phase of an automatic mode of operation may be initiated after/when measured blood glucose concentration for a patient becomes less than a target blood glucose concentration.

Operation 1404 may be implemented in any of numerous manners. Operations 1404a and 1404b include two example approaches to implementing operation 1404, but claimed subject matter is not so limited. By way of example only, at operation 1404a, a continual phase of an automatic mode of operation may be initiated after/when a rate of change of blood glucose concentration for a patient indicates that the blood glucose concentration of the patient is not increasing (e.g., is no longer rising). In other words, initiation of a continual phase may be delayed at least until a rate of change of blood glucose concentration of a patient indicates that the blood glucose concentration of the patient is not increasing. Alternatively, but also by way of example only, at operation 1404b, a continual phase of an automatic mode of operation may be initiated after/when a rate of change of blood glucose concentration for a patient becomes negative. In other words, a continual phase of an automatic mode of operation may be initiated after/when a rate of change of blood glucose concentration for a patient indicates that the blood glucose concentration of the patient is decreasing. Hence, initiation of a continual phase may be delayed at least until a rate of change of blood glucose concentration of a patient indicates that the blood glucose concentration of the patient is decreasing.

In certain example embodiments, when a device is placed into a closed-loop mode, a start up sequence may depend on a history of insulin bolus(es) (e.g., through IOB), a current measured blood glucose concentration, a rate of change for measured blood glucose concentration, combinations thereof, and so forth. In a particular example implementation, a start of continual automatic closed-loop operation may be delayed if blood glucose levels are rising (e.g., if a device is initiated within an early prandial period). Also, correction bolus(es) may be delivered as appropriate to bring a measured blood glucose concentration in line with a targeted blood glucose level in a more expedient manner.

Calculation of correction bolus(es) may consider a current measured blood glucose concentration. Alternatively, correction bolus calculation(s) may include other and/or additional information. For example, a correction bolus amount may be increased or decreased in dependence on a rate of change of measured blood glucose concentration. Insulin-on-board may be included in such calculations so as to incorporate knowledge of prior insulin delivery. If an amount of calculated bolus is less than a predetermined minimum bolus amount (e.g., 0.5-1.5 U, such as 1 U), the effect may likely not be significant, so in such cases delivery may be omitted.

In certain example implementations, continual automatic closed-loop control of insulin delivery may be postponed until measured blood glucose concentration levels are falling by enforcing delays. If a correction bolus is given, it is known from pharmacokinetics and pharmacodynamics of subcutaneously-infused insulin that it may take time to show an appreciable effect on a body; consequently, it is reasonable to enforce longer wait periods. Once one or more predetermined conditions are met to engage continual automatic closed-loop insulin delivery, an initial reference trajectory to target for blood glucose concentration may be set. Such an initial trajectory may be established with an aim, for example, of preventing a control algorithm from being overly-aggressive if measured blood glucose levels might still measure relatively high.

Figure 15A:
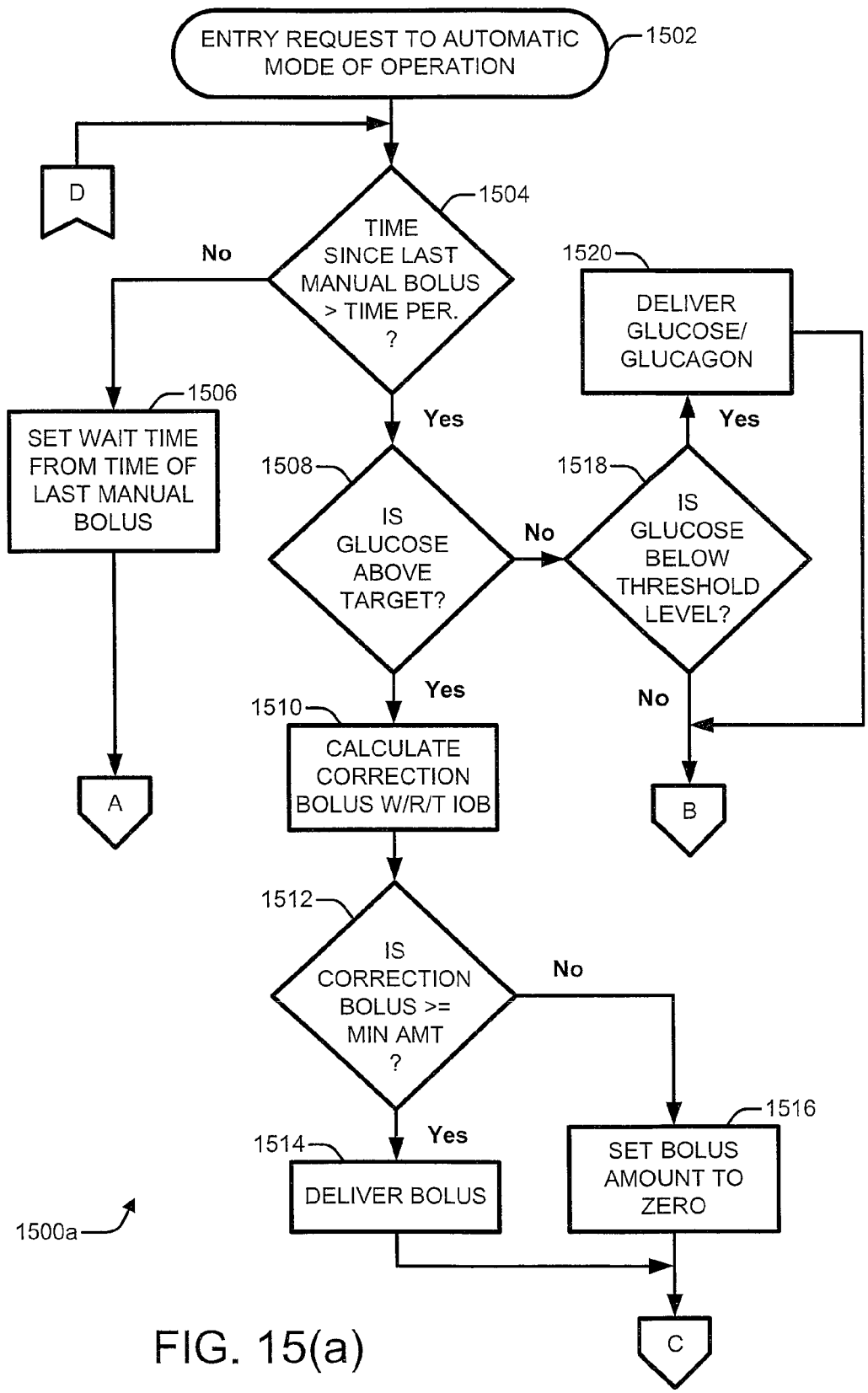
FIGS. 15(a) and 15(b) jointly form a flow diagram of a more specific example method for controlling entry into an automatic mode of operation based on a detected rate of change of blood glucose concentration in accordance with an embodiment.
Figure 15B:
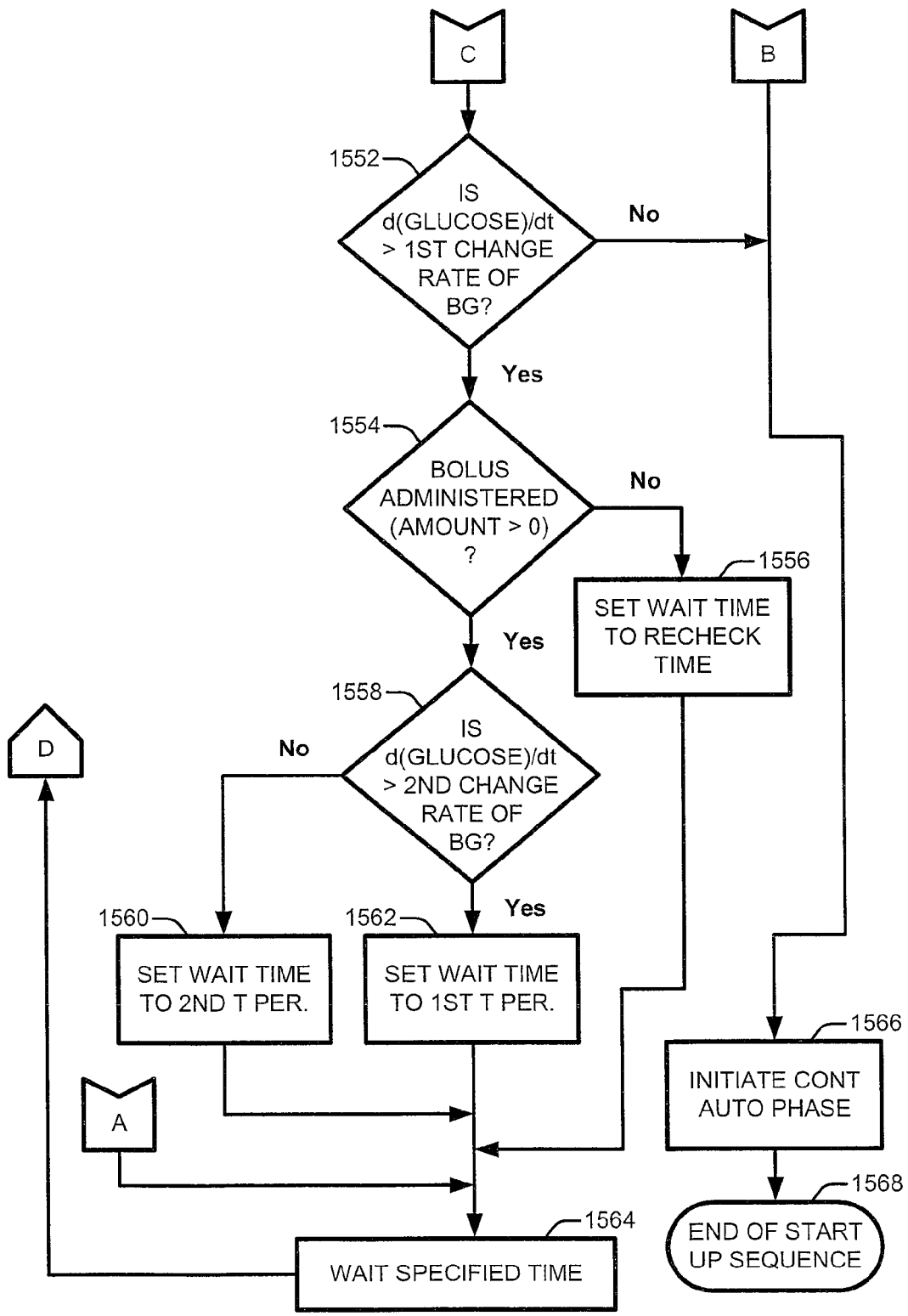

FIGS. 15(a) and 15(b) jointly form a flow diagram 1500 of a more specific example method for controlling entry into an automatic mode of operation based on a detected rate of change of blood glucose concentration in accordance with an embodiment. As illustrated, flow diagram 1500a of FIG. 15(a) includes ten operations 1502-1520. Flow diagram 1500b of FIG. 15(b) includes nine operations 1552-1568. Although specific example values are given in the description below of FIGS. 15(a) and 15(b) for particular embodiments, claimed subject matter is not so limited.

For certain example embodiments, at operation 1502, a controller may receive a request for entry to an automatic mode of operation (e.g., a closed loop operation). At operation 1504, a determination may be made as to whether a time since a last manual bolus of insulin was delivered is greater than a predetermined time period (e.g., 45 minutes). Although 45 minutes is used as an example value, alternative values may be employed, especially those that reflect a time period for an insulin bolus to be substantially cleared in or from a body. Such a time period may be adjusted based, at least in part, on an amount of insulin in a bolus that was delivered, a size of a patient, a known/estimated rate of insulin clearing for patients generally and/or a specific patient, combinations thereof, and so forth, just to name a few examples.

If an elapsed time since a last manual bolus is not greater than a predetermined time period (as determinable at operation 1504), at operation 1506, a wait time may be set (e.g., of 45 minutes) from a time at which a last manual bolus was delivered. Another value for a wait time instead of 45 minutes may alternatively be used. Flow diagram 1500 may continue with FIG. 15(b) at connector "A". If, on the other hand, an elapsed time since a last manual bolus is greater than a predetermined time period (as determinable at operation 1504), at operation 1508 a determination may be made as to whether a blood glucose concentration is above a predetermined target blood glucose concentration level. If not, a determination may be made at operation 1518 as to whether a blood glucose concentration is below a threshold glucose concentration level (e.g., a threshold glucose concentration floor).

At operation 1518, a determination may be made as to whether a blood glucose concentration is below a threshold glucose concentration level. This threshold level may be below a predetermined target blood glucose concentration level. If not, flow diagram 1500 may continue with FIG. 15(*b*) at connector "B". If blood glucose concentration is below a threshold level (as determinable at operation 1518), then glucose and/or glucagon may be delivered to a patient at operation 1520. For example, a bolus of glucose may be delivered intravenously and/or a bolus of glucagon may be delivered to subcutaneous tissue via ISF. Alternatively and/or additionally, glucose and/or glucagon may be delivered by initiating infusion. Other delivery approaches may also be employed instead. After delivery of glucose and/or glucagon, flow diagram 1500 may continue with FIG. 15(*b*) at connector "B".

If, on the other hand, blood glucose concentration is above a predetermined target blood glucose concentration level (as determinable at operation 1508), then at operation 1510 a correction bolus of insulin may be calculated, for example with respect to an amount of insulin on board (IOB) (e.g., an amount of insulin that has been provided to a body that is estimated to have not yet been cleared). At operation 1512, it may be determined whether a calculated correction bolus is greater than a predetermined minimum bolus amount (e.g., greater than (or equal to) 1.0 international unit (IU) of insulin, sometimes abbreviated "U").

If a calculated bolus of insulin is greater than a predetermined minimum bolus amount (as determinable at operation 1512), a bolus of insulin as calculated may be delivered at operation 1514. On the other hand, if a calculated bolus is less than a predetermined minimum bolus amount, a bolus amount may be set to zero (e.g., no bolus need be delivered or bolus delivery is omitted) at operation 1516. Once a bolus of insulin is selectively administered (at operation 1514 or 1516), flow diagram 1500 may continue with FIG. 15(*b*) at connector "C".

From connector "C" of FIG. 15(*b*), at operation 1552, it may be determined whether a derivative of blood glucose concentration with respect to time is greater than a first predetermined rate of change of blood glucose concentration (e.g., greater than negative 0.25 mg/dL/min). For example, it may be determined whether a detected rate of change of blood glucose concentration of a patient indicates that blood glucose concentration of the patient is decreasing. Thus, it may be determined whether a detected rate of change of blood glucose concentration of a patient indicates that blood glucose concentration of the patient does not exceed a first predetermined rate of blood glucose change. Such a first predetermined rate of blood glucose change may differ from negative 0.25 mg/dL/min; it may also be negative or positive. By way of example but not limitation, a first predetermined rate of blood glucose change may be from approximately +1 to −1 mg/dL/min, but claimed subject matter is not so limited.

If a derivative of blood glucose concentration with respect to time is not greater than a first predetermined rate of change of blood glucose concentration (as determinable at operation 1552) (e.g., detected blood glucose concentration is falling), flow diagram 1500 may continue to operation 1566 to initiate a continual automatic phase of an automatic mode of operation (e.g., to start closed-loop control). As full closed-loop control is started upon initiation of a continual automatic phase, a start-up sequence may be considered to end at operation 1568. As indicated by connector "B" on FIGS. 15(*a*) and 15(*b*), if blood glucose concentration is not below a predetermined threshold level (as determinable at operation 1518 of FIG. 15(*a*)) or if glucose and/or glucagon is delivered (at operation 1520 of FIG. 15(*a*)), a continual automatic phase of an automatic mode of operation may be initiated at operation 1568.

If, on the other hand, a derivative of blood glucose concentration with respect to time is greater than a first predetermined rate of change of blood glucose concentration (as determinable at operation 1552) (e.g., detected blood glucose concentration is rising or not definitively falling), it may be ascertained at operation 1554 whether a correction bolus of insulin was administered (at operation 1514 of FIG. 15(*a*)) (e.g., whether a calculated bolus amount is greater than zero from operation 1510). If not, a wait time may be set to be a predetermined recheck time (e.g., one minute) at operation 1556 (e.g., because no new bolus is being cleared). At operation 1564, the specified time is waited. Such waiting may therefore delay starting of full closed-loop control (or, more generally, delay initiation of a continual phase of an automatic mode of operation).

If a correction bolus was administered (e.g., a calculated bolus amount is greater than zero) (as determinable at operation 1554), at operation 1558 it may be determined whether a derivative of blood glucose concentration with respect to time is greater than a second predetermined rate of change of blood glucose concentration (e.g., greater than positive 0.25 mg/dL/min). For example, it may be determined whether a detected rate of change of blood glucose concentration of a patient indicates that blood glucose concentration of the patient is increasing. Thus, it may be determined whether a detected rate of change of blood glucose concentration of a patient indicates that blood glucose concentration of the patient does not exceed a second predetermined rate of blood glucose change. By way of example but not limitation, a second predetermined rate of blood glucose change may be from approximately +1 to −1 mg/dL/min, but claimed subject matter is not so limited. For instance, a first predetermined rate of blood glucose change and/or a second predetermined rate of blood glucose change may be set so as to facilitate a determination as to whether blood glucose concentration is approximately rising, approximately falling, not necessarily rising or falling (e.g., oscillating, currently undetermined, steady, etc.), and so forth.

If a derivative of blood glucose concentration with respect to time is greater than a second predetermined rate of change of blood glucose concentration (as determinable at operation 1558) (e.g., detected blood glucose concentration is rising), a wait time may be set at operation 1562 to a first predetermined time period (e.g., 90 minutes). If, on the other hand, a derivative of blood glucose concentration with respect to time is not greater than a second predetermined rate of change of blood glucose concentration (as determinable at operation 1558) (e.g., detected blood glucose concentration is near zero and/or of an undetermined trend—not necessarily clearly rising or clearly falling), a wait time may be set at operation 1560 to a second predetermined time period (e.g., 45 minutes).

By way of example but not limitation, a first predetermined time period and a second predetermined time period may be set to different time periods than 90 minutes and 45 minutes, respectively. By way of example but not limitation, a first predetermined time period may be set between approximately 60 and 120 minutes. Similarly, by way of example but not limitation, a second predetermined time period may be set between approximately 30 and 60 minutes. Here, a first predetermined time period may be set to any reasonable value that may reflect a time for a body to clear a bolus of insulin when glucose is still rising, and a second predetermined time period may be set to any reasonable value that may reflect a time for a body to clear a bolus of insulin if it is uncertain as to the status of blood glucose change (e.g., it may be rising, falling, nearly flat, etc.). It should be understood that alternative values and approaches may be used without departing from claimed subject matter.

As described above, wait times of different lengths may be set by operations 1556, 1560, and/or 1562. At operation 1564, a specified time may be waited. For example, progression of a method of flow diagram 1500, or operation(s) thereof, may be delayed until a specified wait time expires. Upon expiration of a specified wait time, flow diagram 1500 may continue with FIG. 15(a) at connector "D". In such example manner(s), initiation of a continual phase of an automatic mode of operation may be delayed.

Example Control System Implementations

A controller may be realized for particular example embodiments using any one or more different control algorithm techniques. For instance, controller 12 of FIG. 16 is shown as an example PID controller. Hence, although certain non-exhaustive example embodiments are described herein with regard to a PID controller, other control algorithms may be implemented with a controller.

FIG. 16 is a block diagram of an example closed loop system to control blood glucose levels using a proportional-integral-derivative (PID) control algorithm through at least insulin infusion based on glucose level feedback in accordance with an embodiment. In particular example embodiments, a closed loop control system may be used for delivering insulin to a body to compensate for p-cells that perform inadequately. There may be a desired basal blood glucose level $G_B$ for a particular body. A difference between a desired basal blood glucose level $G_B$ and an estimate of a present blood glucose level G is the glucose level error $G_E$ that may be corrected. For particular example embodiments, glucose level error $G_E$ may be provided as an input to controller 12, as shown in FIG. 16.

For certain example embodiments that are described with reference to FIG. 16, controller 12 may be realized as a PID controller. In example implementations, PID controller gains $K_P$, $K_I$, and/or $K_D$ may be selected so that commands from a controller 12 direct insulin delivery system 64 to release insulin 24 into body 20 at a particular rate. Such a particular rate may cause insulin concentration in blood to follow a similar concentration profile as would be caused by fully functioning human β-cells responding to blood glucose concentrations in a body. Similarly, controller gains $K_P$, $K_I$, and/or $K_D$ may be selected so that commands from controller 12 direct glucagon delivery system 63 to release glucagon 23 in response to relatively low glucose levels. Likewise, controller gains $K_P$, $K_I$, and/or $K_D$ may be selected so that commands from controller 12 direct glucose delivery system 65 to release glucose 25 in response to insulin excursions. In particular example embodiments, controller gains may be selected by observing insulin response(s) of a number of normal glucose tolerant (NGT) individuals having healthy, normally-functioning 3-cells. It should be understood, however, that claimed subject matter is not so limited and that controller 12 may be realized in alternative manners, such as with other PID controller implementations, other types of controllers, and so forth, just to name a few examples.

If glucose level error $G_E$ is positive (meaning, e.g., that a present estimate of blood glucose level G is higher than a desired basal blood glucose level $G_B$), then a command from controller 12 may generate a PID command to drive insulin delivery system 64 to provide insulin 24 to body 20. Insulin delivery system 64 may be an example implementation of insulin delivery system 14 (e.g., of FIG. 1). Likewise, if $G_E$ is negative (meaning, e.g., that a present estimate of blood glucose level G is lower than a desired basal blood glucose level $G_B$), then a command from controller 12 may generate a PID command to drive glucagon delivery system 63 to provide glucagon 23 to body 20. Glucagon delivery system 63 may be an example implementation of glucagon delivery system 13 (e.g., of FIG. 1). Similarly, if $G_E$ is negative (meaning, e.g., that a present estimate of blood glucose level G is lower than a desired basal blood glucose level $G_B$), then a command from controller 12 may generate a PID command to drive glucose delivery system 65 to provide glucose 25 to body 20. Glucose delivery system 65 may be an example implementation of glucose delivery system 15 (e.g., of FIG. 1). As shown in FIG. 16, insulin 24 and glucagon 23 are delivered via subcutaneous tissue 44; however, they may alternatively be delivered intravenously. If a patient's blood glucose is below a threshold floor level (which may be below a targeted set point or desired basal blood glucose level $G_B$), then glucose and/or glucagon may be delivered to increase the glucose level of the patient.

In terms of a control loop for purposes of discussion, glucose may be considered to be positive, and therefore insulin may be considered to be negative. Sensor 26 may sense an ISF glucose level of body 20 and generate a sensor signal 16. In certain embodiments that are described herein with particular reference to FIG. 16, a control loop may include a filter and calibration unit 456 and/or correction algorithm(s) 454. However, this is by way of example only, and claimed subject matter is not so limited. Sensor signal 16 may be filtered and calibrated at unit 456 to create an estimate of present blood glucose level 452. In particular example embodiments, an estimate of present blood glucose level G may be adjusted with correction algorithms 454 before it is compared to a desired basal blood glucose level $G_B$ to calculate a new glucose level error $G_E$ to start a loop again. Also, an attendant, a caretaker, a patient, etc. may obtain blood glucose reference measurements from a patient's blood using, e.g., glucose test strips. These blood-based measurements may be used to calibrate ISF-based sensor measurements using techniques, e.g., such as those described in U.S. Pat. No. 6,895,263, issued 17 May 2005.

If a glucose level error $G_E$ is negative (meaning, e.g., that a present estimate of blood glucose level is lower than a desired basal blood glucose level $G_B$), then controller 12 may reduce or stop insulin delivery depending on whether an integral component response of a glucose error $G_E$ is still positive. In alternative embodiments, as discussed below, controller 12 may initiate infusion of glucagon 23 and/or glucose 25 if glucose level error $G_E$ is negative. If a glucose level error $G_E$ is zero (meaning, e.g., that a present estimate of blood glucose level is equal to a desired basal blood glucose level $G_B$), then controller 12 may or may not issue commands to infuse insulin 24, glucagon 23, and/or glucose 25, depending on a derivative component (e.g., whether glucose level is raising or falling) and/or an integral component (e.g., how long and by how much glucose level has been above or below basal blood glucose level $G_B$).

To more clearly understand the effects that a body has on such a control loop, a more detailed description of physiological effects that insulin has on glucose concentration in ISF is provided. In particular example embodiments, insulin delivery system 64 may deliver insulin 24 into ISF of subcutaneous tissue 44 (e.g., also of FIGS. 3, 4, and 6) of body 20. Alternatively, insulin delivery system 64 or one or more separate infusion device(s) (e.g., glucagon delivery system 63 and/or glucose delivery system 65) may similarly deliver glucagon 23 into ISF of subcutaneous tissue 44 and/or deliver glucose 25 into an intravenous cavity of a blood stream. Here, insulin and/or glucagon may diffuse from local ISF surrounding a cannula into blood plasma and spread throughout body 20 in a main circulatory system. Infused insulin and/or glucagon may diffuse from blood plasma into ISF substantially throughout the entire body.

Here in the body, insulin 24 may bind with and activate membrane receptor proteins on cells of body tissues. This may facilitate glucose permeation into activated cells. In this way, tissues of body 20 may take up glucose from ISF. As ISF glucose level decreases, glucose may diffuse from blood plasma into ISF to maintain glucose concentration equilibrium. Glucose in ISF may permeate a sensor membrane of sensor 26 and affect sensor signal 16.

In addition, insulin may have direct and indirect effects on liver glucose production. Typically, increased insulin concentration may decrease liver glucose production. Therefore, acute and immediate insulin response may not only help a body to efficiently take up glucose, but it may also substantially stop a liver from adding to glucose in the blood stream. In alternative example embodiments, as pointed out above, insulin, glucagon, and/or glucose may be delivered more directly into the blood stream instead of into ISF, such as by delivery into veins, arteries, the peritoneal cavity, and so forth, just to name a few examples. Accordingly, any time delay associated with moving insulin, glucagon, and/or glucose from ISF into blood plasma may be diminished. In other alternative example embodiments, a glucose sensor may be in contact with blood or other body fluids instead of ISF, or a glucose sensor may be outside of a body such that it may measure glucose through a non-invasive means. Embodiments using alternative glucose sensors may have shorter or longer delays between an actual blood glucose level and a measured blood glucose level.

Example PID Controller Implementations for Example Startup Embodiments

A general equation that is usable for a PID algorithm is given by Equation (1):

$$u(t) = \underbrace{K_P e(t)}_{Proportional} + \underbrace{\frac{K_P}{\tau_I} \int_0^t e(\tau) d\tau}_{Integral} + \underbrace{K_P \tau_D \frac{de(t)}{dt}}_{Derivative} \quad (1)$$

where u(t) may be a manipulated variable used to regulate a system and $e(t) = G_S(t) - T_G(t)$ may be an error signal. An error signal may be a difference between a set point ($T_G(t)$, a target where a controlled variable is desired to be at) and a controlled variable ($G_S(t)$). PID tuning parameters may include a controller gain ($K_P$), an integral time constant ($T_I$), and a derivative time constant ($T_D$). A proportional term adjusts a manipulated variable in proportion to an error at a given time. An integral term adjusts a manipulated variable in proportion to an accumulated error (e.g., modeled by an integral) as averaged over a time period specified by $T_I$. Thus, as $T_I$ is increased, this integral component may have a lesser or lower effect on overall control action. A derivative term adjusts a manipulated variable in proportion to a derivative of an error. Multiplication by $T_D$ can be viewed as a projection of an error into the future if a current rate of change persists; therefore, having a larger $T_D$ may result in a stronger or higher change to the control action.

With a mere conventional transfer approach, an integral term may be calculated such that a control algorithm's infusion rate matches an open-loop basal rate active at a starting time. A control algorithm that is started with a conventional transfer approach may then begin "correcting" from that point to move a glucose level toward a specified target ($T_G$).

For certain example embodiments having a transitional automatic phase, a startup algorithm may also attempt to move a measured glucose concentration to a specified target level. However, in a transitional automatic phase it may further calculate a correction bolus at a starting time that considers not only a current measured blood glucose value, but also an insulin-on-board amount. It may still further consider a rate of change of measured blood glucose concentration. Moreover, a blood glucose reference trajectory may also be specified, e.g., for an expected change in glucose level due to a delivered (manual or automated) correction bolus. Such a reference trajectory (which may be initially rising or falling) may retard or limit an amount of insulin that a controller will deliver (e.g., to reduce or avoid a hypoglycemic event).

If insulin feedback is also incorporated into a PID algorithm, an insulin pharmacokinetic model may be initialized by utilizing prior insulin delivery from a period of open-loop operation of a pump. Such insulin-on-board may also be used to impose additional constraints on controller action, thereby incorporating open-loop history.

Example Embodiments for Specifying a Target Blood Glucose Reference Trajectory

For certain example embodiments, a blood glucose reference trajectory may be based on reasonable performance expectations that are founded on known physiology and pharmacokinetics and pharmacodynamics of insulin. The greater a measured blood glucose concentration is above a targeted blood glucose level, the more likely establishing a blood glucose reference trajectory is to be helpful in avoiding a hypoglycemic event. Many different approaches may be employed to define a blood glucose reference trajectory that is initially rising or falling. Example approaches for defining a reference trajectory to target for blood glucose levels include, but are not limited to: a simple exponential decay curve, a second order response, a model-based expected response from a correction bolus considering starting conditions, a combination thereof, and so forth. After a reference trajectory is established, an automatic mode of operation (e.g., a continual phase thereof) may attempt to cause a measured blood glucose concentration of patient to track the reference trajectory.

Thus, for particular example implementations, a second order response may be used that starts at a glucose level when continual automatic closed-loop control is initiated. A target blood glucose reference trajectory in this case may be described mathematically as shown by Equation (2):

$$T_G(t) = \frac{G_S(t_0) - T_{Gb}}{\tau_1 - \tau_2}(\tau_1 e^{-t/\tau_1} - \tau_2 e^{-t/\tau_2}) + T_{Gb}, \quad (2)$$

where $T_G(t)$ may be a glucose set point as a function of time, $G_S(t_0)$ may be a sensor glucose value at a start of continual automatic closed-loop control ($t_0$), $T_{Gb}$ may be a baseline or relatively fixed glucose target after an initial period, and $T_1$ and $T_2$ may be time constants that define a desired response. Such time constants may be set so that a reference trajectory is adequate from a clinical perspective.

Because this particular reference trajectory is specified analytically in this way, its rate of change can also be derived analytically. This rate of change may be used explicitly in, e.g., a derivative term of a PID algorithm. However, reference trajectories may be implemented in alternative manners.

An initial blood glucose targeted reference trajectory may be rising or falling. Whether a reference trajectory is rising or falling may depend on whether a patient's blood glucose concentration is rising or falling when an automatic mode of operation is activated (e.g., and/or when a continual automatic phase is initiated). An example initially-falling reference trajectory is shown on the right side of the upper graph of FIG. 11. An example initially-rising reference trajectory is shown in FIG. 17.

Figure 17:
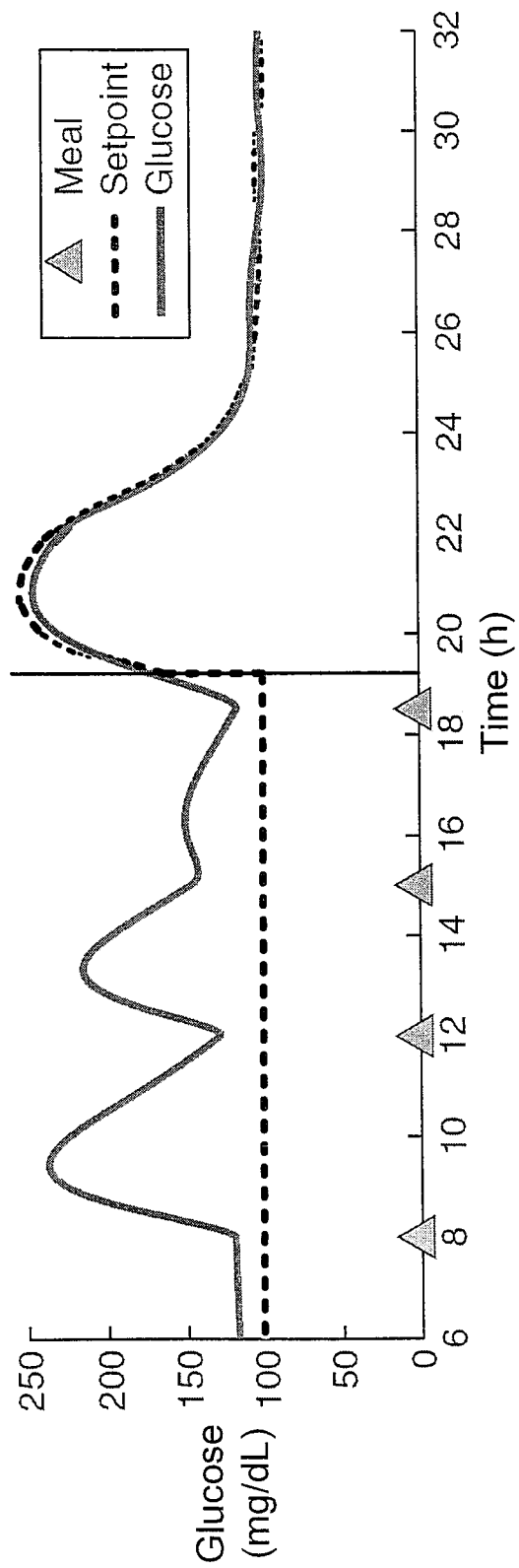
FIG. 17 illustrates a graph that depicts an activation of closed-loop control in conjunction with an example start-up scenario in which an initial upward reference trajectory is established in accordance with an embodiment.

FIG. 17 illustrates a graph 1700 that depicts an activation of closed-loop control in conjunction with an example start-up scenario in which an initial upward reference trajectory is established in accordance with an embodiment. Graph 1700 depicts results for an example simulation when close-loop control is activated at 19:10 hours, as indicated by the vertical line thereat. An abscissa axis represents time in hours from 6 to 32. An ordinate axis represents glucose (mg/dL). Triangles represent meals, the solid line represents a current glucose level, and the dotted line represents a desired or targeted glucose level.

More specifically, an example simulation as illustrated in graph 1700 of FIG. 17 entails a start of closed-loop control at 19:10 h after a 90 g carbohydrate and high fat meal at 18:30 h. A full manual bolus is supplied with the meal at 18:30 h as indicated by the right-most triangle. On the left side of the vertical line, which is located at 19:10 h, the targeted level is a blood glucose concentration constant of 100 mg/dL as represented by the dotted line. On the right side of the vertical line, the targeted level is a blood glucose concentration reference trajectory that is initially rising. As shown, the blood glucose concentration reference trajectory gradually stops rising and begins to fall. A blood glucose concentration of the patient, as represented by the solid line, is made to track the dotted line targeted reference trajectory that initially rises, gradually falls, and eventually reaches a relatively steady-state constant while in an automatic mode of operation.

Alternatively, in situations in which measured blood glucose concentration is substantially close to (e.g., within approximately 15-25% of) a targeted level when a continual automatic phase is initiated, a control algorithm may be started with a fixed set point (e.g., no reference trajectory). If measured blood glucose concentration happens to be below a targeted level when a continual automatic phase is initiated, using a fixed set point is likely to move glucose levels up to a targeted level in a more expedient manner (possibly with delivery of glucose and/or glucagon if measured blood glucose concentration is also below a threshold floor level, as described herein above with particular reference to FIG. 15(a)). However, a different, rising reference trajectory may instead be defined, with clinical aspects for such a below-targeted-glucose-level scenario being taken into account.

Unless specifically stated otherwise, as is apparent from the preceding discussion, it is to be appreciated that throughout this specification discussions utilizing terms such as "processing", "computing", "calculating", "determining", "estimating", "selecting", "identifying", "obtaining", "representing", "receiving", "transmitting", "storing", "analyzing", "associating", "measuring", "detecting", "controlling", "delaying", "initiating", "setting", "delivering", "waiting", "starting", "providing", and so forth may refer to actions, processes, etc. that may be partially or fully performed by a specific apparatus, such as a special purpose computer, special purpose computing apparatus, a similar special purpose electronic computing device, and so forth, just to name a few examples. In the context of this specification, therefore, a special purpose computer or a similar special purpose electronic computing device may be capable of manipulating or transforming signals, which are typically represented as physical electronic and/or magnetic quantities within memories, registers, or other information storage devices; transmission devices; display devices of a special purpose computer; or similar special purpose electronic computing device; and so forth, just to name a few examples. In particular example embodiments, such a special purpose computer or similar may comprise one or more processors programmed with instructions to perform one or more specific functions. Accordingly, a special purpose computer may refer to a system or a device that includes an ability to process or store data in the form of signals. Further, unless specifically stated otherwise, a process or method as described herein, with reference to flow diagrams or otherwise, may also be executed or controlled, in whole or in part, by a special purpose computer.

It should be noted that although aspects of the above systems, methods, devices, processes, etc. have been described in particular orders and in particular arrangements, such specific orders and arrangements are merely examples and claimed subject matter is not limited to the orders and arrangements as described. It should also be noted that systems, devices, methods, processes, etc. described herein may be capable of being performed by one or more computing platforms. In addition, instructions that are adapted to realize methods, processes, etc. that are described herein may be capable of being stored on a storage medium as one or more machine readable instructions. If executed, machine readable instructions may enable a computing platform to perform one or more actions. "Storage medium" as referred to herein may relate to media capable of storing information or instructions which may be operated on, or executed by, one or more machines (e.g., that include at least one processor). For example, a storage medium may comprise one or more storage articles and/or devices for storing machine-readable instructions or information. Such storage articles and/or devices may comprise any one of several media types including, for example, magnetic, optical, semiconductor, a combination thereof, etc. storage media. By way of further example, one or more computing platforms may be adapted to perform one or more processes, methods, etc. in accordance with claimed subject matter, such as methods, processes, etc. that are described herein. However, these are merely examples relating to a storage medium and a computing platform and claimed subject matter is not limited in these respects.

Although there have been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from central concepts that are described herein. Therefore, it is intended that claimed subject matter not be limited to particular examples disclosed, but that such claimed subject matter may also include all aspects falling within the scope of appended claims, and equivalents thereof.

What is claimed is:

1. An apparatus comprising:
   a controller to receive one or more signals based on glucose sensor measurements, said controller comprising one or more processors to:
   detect a request for entry of an automatic mode of operation of a glucose monitoring and insulin delivery system for a patient; and
   control said entry of said automatic mode of operation based, at least in part, on a detected rate of change of blood glucose concentration of the patient by delaying initiation of a continual phase of said automatic mode of operation at least until said detected rate of change of blood glucose concentration of the patient is less than a predetermined rate of blood glucose change.

2. The apparatus of claim 1, further comprising:
one or more glucose sensors adapted to be coupled to a patient to obtain glucose sensor measurements and adapted to provide said one or more signals based on said glucose sensor measurements,
wherein said detected rate of change of blood glucose concentration is based, at least in part, on measurements obtained from said one or more glucose sensors.

3. The apparatus of claim 1, wherein said controller is capable of controlling said entry by delaying initiation of said continual phase of said automatic mode of operation at least until said detected rate of change of blood glucose concentration of the patient indicates that the blood glucose concentration of the patient is not increasing.

4. The apparatus of claim 1, wherein said controller is capable of further controlling said entry by: establishing a reference trajectory for a set point of said automatic mode of operation; initiating a continual phase of said automatic mode of operation; and attempting to cause a measured blood glucose concentration of the patient to track said reference trajectory.

5. The apparatus of claim 1, wherein said controller is capable of controlling said entry by determining a time at which to exit a transitional phase of said automatic mode of operation and enter a continual phase of said automatic mode of operation.

6. The apparatus of claim 5, wherein said one or more processors of said controller are further to:
provide insulin in accordance with a basal rate and deliver at least one bolus of insulin in accordance with measured blood glucose concentration of the patient during said transitional phase of said automatic mode of operation; and
provide insulin in accordance with said current measured blood glucose concentration of the patient during said continual phase of said automatic mode of operation.

7. The apparatus of claim 6, wherein said at least one bolus of insulin is delivered using a relatively discrete mechanism during said transitional phase, and said insulin is provided using a relatively continual mechanism during said continual phase in accordance with a control algorithm.

8. The apparatus of claim 1, wherein said one or more processors of said controller are further to: selectively delay initiation of a continual phase of said automatic mode of operation based on a length of time that has elapsed since a most-recent manual delivery of a bolus of insulin; and selectively delay initiation of said continual phase of said automatic mode of operation while a measured blood glucose concentration of the patient is increasing as determined from said detected rate of change of blood glucose concentration of the patient.

9. The apparatus of claim 1, wherein said controller is capable of controlling said entry by delivering at least one of glucose or glucagon to the patient if a measured blood glucose concentration of the patient is less than a threshold glucose concentration level.

10. An apparatus comprising:
a controller to receive one or more signals based on glucose sensor measurements, said controller comprising one or more processors to:
detect a request for entry of an automatic mode of operation of a glucose monitoring and insulin delivery system for a patient; and
control said entry of said automatic mode of operation by delaying initiation of a continual phase of said automatic mode of operation until at least a predetermined length of time has elapsed since a most-recent manual delivery of a bolus of insulin.

11. An apparatus comprising:
a controller to receive one or more signals based on glucose sensor measurements, said controller comprising one or more processors to:
detect a request for entry of an automatic mode of operation of a glucose monitoring and insulin delivery system for a patient; and
control said entry of said automatic mode of operation by initiating a continual phase of said automatic mode of operation if a measured blood glucose concentration of the patient does not exceed a target blood glucose concentration for the patient.

12. An apparatus comprising:
a controller to receive one or more signals based on glucose sensor measurements, said controller comprising one or more processors to:
detect a request for entry of an automatic mode of operation of a glucose monitoring and insulin delivery system for a patient; and
control said entry of said automatic mode of operation by:
calculating a correction bolus of insulin based, at least in part, on an insulin-on-board value and a target blood glucose concentration for the patient; and
delivering said correction bolus of insulin to the patient if an amount of said correction bolus of insulin exceeds a predetermined minimum bolus amount.

13. The apparatus of claim 12, wherein said controller is capable of calculating said correction bolus of insulin by calculating said correction bolus of insulin based, at least in part, on said detected rate of change of blood glucose concentration of the patient.

14. An apparatus comprising:
a controller to receive one or more signals based on glucose sensor measurements, said controller comprising one or more processors to:
detect a request for entry of an automatic mode of operation of a glucose monitoring and insulin delivery system for a patient; and
control said entry of said automatic mode of operation by initiating a continual phase of said automatic mode of operation if said detected rate of change of blood glucose concentration of the patient does not exceed a first predetermined rate of blood glucose change.

15. The apparatus of claim 14, wherein said controller is further capable of controlling said entry by:
waiting a predetermined period of time if said detected rate of change of blood glucose concentration of the patient exceeds said first predetermined rate of blood glucose change; and
after expiration of said predetermined period of time, determining if a correction bolus of insulin is to be delivered based, at least in part, on an insulin-on-board value.

16. The apparatus of claim 14, wherein said controller is further capable of controlling said entry by: comparing said detected rate of change of blood glucose concentration of the patient to a second predetermined rate of blood glucose change if said detected rate of change of blood glucose concentration of the patient exceeds said first predetermined rate of blood glucose change; if said detected rate of change of blood glucose concentration of the patient exceeds said second predetermined rate of blood glucose change, waiting a first predetermined period of time; if said detected rate of change of blood glucose concentration of the patient does not exceed said second predetermined rate of blood glucose change, waiting a second predetermined period of time; and after expiration of said first or second predetermined period of time, determining if a measured blood glucose concentration of the patient exceeds a target blood glucose concentration for the patient.

17. An apparatus comprising:
a controller to receive one or more signals based on glucose sensor measurements, said controller comprising one or more processors to:
detect a request for entry of an automatic mode of operation of a glucose monitoring and insulin delivery system for a patient; and
control said entry of said automatic mode of operation by:
delaying initiation of a continual phase of said automatic mode of operation until at least a predetermined length of time has elapsed since a most-recent manual delivery of a bolus of insulin; and
after at least said predetermined length of time has elapsed, initiating said continual phase of said automatic mode of operation after a measured blood glucose concentration of the patient is less than a target blood glucose concentration for the patient.

18. The apparatus of claim 17, wherein said controller is capable of controlling said entry by: after at least said predetermined length of time has elapsed, initiating said continual phase of said automatic mode of operation after said detected rate of change of blood glucose concentration of the patient becomes less than a predetermined rate of blood glucose change.

19. The apparatus of claim 18, wherein said controller is capable of controlling said entry by: after at least said predetermined length of time has elapsed, initiating said continual phase of said automatic mode of operation after said detected rate of change of blood glucose concentration of the patient becomes negative.

* * * * *